(12) United States Patent
Baron

(10) Patent No.: US 11,004,562 B2
(45) Date of Patent: May 11, 2021

(54) PROGRAMMABLE MEDICAL DEVICES

(71) Applicant: X-CARDIO CORP. KK, Tokyo (JP)

(72) Inventor: Ehud Baron, Tokyo (JP)

(73) Assignee: X-CardioCorp. KK, Tokyo (JP)

(*) Notice: Subject to any disclaimer, the term of this patent is extended or adjusted under 35 U.S.C. 154(b) by 0 days.

(21) Appl. No.: 16/103,422

(22) Filed: Aug. 14, 2018

(65) Prior Publication Data
US 2018/0353127 A1 Dec. 13, 2018

Related U.S. Application Data

(63) Continuation of application No. 14/395,624, filed as application No. PCT/GB2013/050717 on Mar. 20, 2013, now abandoned.

(30) Foreign Application Priority Data

Mar. 20, 2012 (GB) .................................... 1204831

(51) Int. Cl.
G16H 40/67 (2018.01)
A61B 5/00 (2006.01)
G16H 40/63 (2018.01)
G16H 40/40 (2018.01)
A61B 8/08 (2006.01)
(Continued)

(52) U.S. Cl.
CPC ............. *G16H 40/67* (2018.01); *A61B 3/165* (2013.01); *A61B 5/0024* (2013.01); *A61B 5/0205* (2013.01); *A61B 5/02216* (2013.01); *A61B 5/316* (2021.01); *A61B 5/318* (2021.01); *A61B 5/341* (2021.01); *A61B 5/4839* (2013.01); *A61B 5/7485* (2013.01); *A61B 8/0808* (2013.01); *A61B 8/0883* (2013.01);
*A61B 8/483* (2013.01); *A61B 8/488* (2013.01); *A61B 8/565* (2013.01); *A61M 5/1723* (2013.01); *G16H 20/17* (2018.01); *G16H 30/40* (2018.01); *G16H 40/40* (2018.01); *G16H 40/63* (2018.01);
(Continued)

(58) Field of Classification Search
CPC ..................................................... A61B 5/0024
See application file for complete search history.

(56) References Cited

U.S. PATENT DOCUMENTS 6,478,739 B1* 11/2002 Hong .................... A61B 8/4494
600/437
7,326,180 B2* 2/2008 Tanabe ..................... A61B 5/02
600/300
(Continued)

OTHER PUBLICATIONS

Rajiv Chakravort: "MobiCare: A Programmable Service Architecture for Mobile Medical Care", Proceedings of UbiCare 2006, Mar. 31, 2006 (Mar. 31, 2006 ), XP055067045, Retrieved from the Internet: URL:http://pages.cs.wisc.edu/~rajiv/pubs/care.pdf [retrieved on Jun. 24, 2017].

Primary Examiner — John R Downey
(74) Attorney, Agent, or Firm — William Dippert; Laurence Greenberg; Werner Stemer

(57) ABSTRACT

A patient data capture and processing system that comprises general programmable medical device (GPMD) and a patient medical device controller (PPS). The patient server is configured to program the function data store of the GPMD, and obtain the data acquired by the GPMD, via the communications connection, wherein the data is stored in patient data records, and wherein the patient server is further configured to extract and output clinically significant events.

17 Claims, 13 Drawing Sheets

(51) Int. Cl.
*A61B 8/00* (2006.01)
*G16H 20/17* (2018.01)
*G16H 30/40* (2018.01)
*A61B 5/316* (2021.01)
*A61B 5/318* (2021.01)
*A61B 5/341* (2021.01)
*A61B 3/16* (2006.01)
*A61B 5/0205* (2006.01)
*A61B 5/022* (2006.01)
*A61M 5/172* (2006.01)
*A61B 8/06* (2006.01)
*A61B 8/13* (2006.01)
*A61B 5/021* (2006.01)

(52) U.S. Cl.
CPC .............. *A61B 5/0006* (2013.01); *A61B 5/021* (2013.01); *A61B 8/06* (2013.01); *A61B 8/13* (2013.01); *A61B 2560/0443* (2013.01); *A61B 2562/08* (2013.01)

(56) References Cited

U.S. PATENT DOCUMENTS

| | | | |
|---|---|---|---|
| 7,883,478 B2* | 2/2011 | Skinner | A61G 7/05769 |
| | | | 5/655.3 |
| 9,357,921 B2* | 6/2016 | Chang | A61B 5/00 |
| 2006/0047538 A1 | 3/2006 | Condurso et al. | |
| 2009/0005657 A1* | 1/2009 | Bodlaender | A61B 5/00 |
| | | | 600/301 |
| 2009/0149721 A1* | 6/2009 | Yang | A61B 5/0002 |
| | | | 600/301 |
| 2009/0319192 A1 | 12/2009 | Bergner et al. | |
| 2011/0121976 A1* | 5/2011 | Johns | A61B 3/113 |
| | | | 340/576 |
| 2011/0208013 A1 | 8/2011 | Phan et al. | |
| 2011/0245623 A1 | 10/2011 | Chutani et al. | |
| 2011/0282168 A1* | 11/2011 | Weiss | A61B 5/742 |
| | | | 600/323 |

* cited by examiner (Prior Art - seperate medical devices)

PROGRAMMABLE MEDICAL DEVICES

CROSS-REFERENCE TO RELATED APPLICATIONS

This patent application is a continuation of co-pending U.S. patent application Ser. No. 14/395,624, filed Oct. 20, 2014, which is a National Stage filing under 35 U.S.C. § 371 of International Patent Application No. PCT/GB2013/050717, filed Mar. 20, 2013, which is based upon and claims the priority date of British Patent Application No. 1204831.0, filed Mar. 20, 2012, each of which is incorporated herein in its entirety.

FIELD OF THE INVENTION

This invention relates to medical devices.

BACKGROUND TO THE INVENTION

Hospitals today use a large number of medical devices that are exploited only a fraction of the time, consume a lot of space and are difficult to maintain and even more to upgrade and add features. Medical devices typically include an analogue part, hardware to convert analogue data to digital signals, a processor, display and user interface.

Today medical devices are designed to fulfill a specific function, such as measurement of a specific parameter (e.g., blood pressure), monitoring a specific parameter (e.g., ECG), provide imaging using magnetic fields, ultrasound, X-Ray, etc., or performing a treatment like infusion pump for drug delivery. For these purposes, each device has suitable circuitry and dedicated sensors (sense a signal) and effectors (to deliver an action/response).

In recent years, there have been efforts to use general purpose devices such as personal computers or smartphones in combination with dedicated hardware to create new medical devices. An example of this has been created by Withings which uses a cuff including the circuitry of a blood pressure (BP) monitor without a display and user interface. This circuitry that includes the air-pump and pressure sensor plugs directly into a smartphone or tablet computer such as iPhone™ or iPad™. The software application reads the wearer's blood pressure and heart rate and then sends the data to a doctor or synchronizes directly with electronic medical record systems such as Google Health and Microsoft HealthVault. Another example is IHealth's Blood Pressure Monitoring System, which provides a similar connected blood pressure cuff. Smartphone accessories are available for use specifically by doctors. The PhoneOximeter, for example, developed by the University of British Columbia, measures blood oxygen levels and may be used in developing countries to safely administer anesthesia. Another example, implemented on a smartphone, is provided by Mobisante Inc. for ultrasonic imaging in U.S. patent application Ser. No. 2011/0245632.

Conventional approaches to use of general purpose hardware must be augmented with additional hardware to perform as a medical device. There is therefore a need to address this problem in order to provide devices more capable of providing a range of medical functionality.

Sensors are used to obtain data from a patient being monitored. Examples of sensor technology concepts include U.S. patent application Ser. No. 20070287925 by Tensys Medical which discloses a wrist device with self positioning BP sensor. Such a device adjusts compression for the vessel by using dynamically applied dither perturbations (e.g., modulation) on the various axes associated with the vessel.

In U.S. Pat. No. 8,038,619 a motor driver for ultrasound system is provided. The ultrasound system includes a transmitter and receiver, both communicatively coupled to a transducer array of an ultrasound probe. The ultrasound system further includes a digital motor driver for controlling movement of the transducer array.

Multigon Industries, Inc. demonstrates a robotic headband. This product is headgear that performs auto-tracking of the ultrasound Doppler signals from the arteries in the brain. The ROBOTOC2MD locks on to the signal and maintains it despite patient or headgear movement. A similar product is also provided by Shenzen Delicate Electronics Co., Ltd.

Both the Tensys Medical BP sensor and Multigon/Delicate robotic headgear are examples of self positioning sensors (automatically adjustable sensors).

Sensors Plug&Play (TEDS) Architecture:

Sensors Plug&Play, based on the IEEE 1451.4 (TEDS) standard, brings plug-and-play capabilities to transducers and is shown in FIGS. 9a and 9b. With plug-and-play technology, you can store a TEDS directly on a sensor. TEDS-compatible measurement systems can autodetect and automatically configure these "smart sensors" for measurement, reducing setup time and eliminating transcription errors that commonly occur during sensor configuration.

With virtual TEDS technology, one can configure traditional analogue sensors (with an adaptor using mixed mode). You can use each electronic file to store the identification, configuration, and calibration information for an individual sensor. In most cases, these files are stored in a database where you can easily download them and use them to configure a sensor for measurement.

Examples of sensors are:
Class I Sensor Measurements
  Accelerometers and Microphones
    +−0.316 mV to 42.4 V input range
    IEPE conditioning, software-configurable
    204.8 kS/s maximum sampling rate
    118 dB dynamic range, 24-bit resolution
Class II Sensor Measurements
  Bridge Sensors
    Load, force, pressure, torque
    Direct sensor connectivity
    Programmable excitation
    Programmable filter per channel
  Strain Gages
    Quarter, half, full bridge support
    Programmable excitation (0-10 V)
    Programmable filter per channel
    Programmable gain per channel
  Voltage Sensors
    Custom sensor-specific scaling
    Programmable gain
    Isolated inputs
    Programmable filter per channel
  RTDs and Thermistors
    2, 3, and 4-wire sensor inputs
    1 mA excitation source
    30 Hz lowpass filter per channel
    Custom sensor connectivity
  Thermocouples
    Onboard cold-junction compensation
    2 Hz lowpass noise filter per channel
    Open-thermocouple detection
    Customer sensor connectivity FIG. 1a shows how medical devices, including sensor devices and effector devices, are operated today in a medical environment. In FIG. 1a there are examples of three independent medical devices in use around the patient: a vital signs monitor 100, an infusion pump 110 and an ultrasound imaging device 115.

The vital signs monitor 100 includes a display 102, a set of analogue amplification modules 104 and several independent devices such as electrocardiogram (ECG) 108, Pulse Plethysmo-Graphy (PPG) 106, Invasive Blood Pressure (IBP) 107, and the like. The corresponding analogue electrodes 105 connect to each module. E.g., ECG electrodes 108 to the ECG modules, inflatable cuff 107 to the NIBP module, optical photodiodes and LED 106 to the PPG. The vital signs monitor 100 includes also a user interface that is not depicted in FIG. 1a.

The infusion pump 110 (which is an example of an effector device, or more specifically a treatment device) also includes a small display, control unit for controlling the pump, and the pump itself. In addition, it has a user interface for manual control of the pump by the doctor or nurse.

An imaging device is also shown. In FIG. 1a this is a portable ultrasound imaging device 115. The Ultrasound imaging 115 has its own display 116, a signal processing unit and a beam former that is connected to the ultrasonic probe.

Each one of the many devices around the patient has its own display, processing unit, User Interface, etc. There is no communication among them and even inside the vital signs monitor 100, each channel 104 (ECG, NIBP, PPG and the like) works independently. As will be appreciated, as each of these devices is operating independently, there is also no mechanism by which data can be shared between such devices.

In GB1120345.2 which is herein incorporated by reference, there is a description of a Patient Server or Medical Console. The Patient Server depicted in FIG. 1b connects to all the medical devices around a patient using a single display and User Interface.

FIG. 1b taken from British Patent Application GB1120345.2 shows an overview of the Patient Server (medical console) and its associated network of medical devices (sensor devices and effector devices) coupled to the Patient Server. By comparison to the example in FIG. 1a, which shows the existing situation of employing independent medical devices (such as a Vital Signs Monitor 100, an Infusion pump 110, and an ultrasound imaging 115), all these devices are now coupled to the Patient Server. The Patient Server 120 processes all signals and uses one display 118 and a shared User Interface Controller 119 for controlling, managing and configuring all the medical devices attached.

SUMMARY OF THE INVENTION

According to a first aspect of the invention there is provided a patient data capture and processing system, the system comprising: a programmable, platform medical device, the device comprising: at least one patient sensor interface; a processor coupled to said sensor interface and to a communications interface; programmable memory, coupled to said processor, wherein said memory is programmable via said communications interface to define a plurality of different patient sensing functions to implement, in software, a plurality of different medical devices; said memory further storing code for said processor to send medical device data captured from a said patient sensing function via said communications interface over a communications connection; a patient medical device controller, comprising: a further communications interface coupled to said communications connection; a processor; memory, coupled to said processor, storing signal processing code to retrieve said medical device data from one or more of said programmable platform medical devices via said communications connection, to filter clinically significant events from said retrieved medical device data to detect clinically significant events, and to output said filtered data for one or both of storage and review by a physician.

The data capture and processing system includes at least one programmable platform medical device (or general purpose medical device (GPMD)) and a patient medical device controller (a Patient Server (PPS)), which are connected by a communications connection, such as a network connection, for example. The GPMD is programmable to implement a plurality of different medical devices, meaning that the same platform can be reused for different medical devices. The GPMD may be programmable via a communications interface to define the patient sensing functions to implement and, in use, any collected data may be communicated to the Patient Server via the communications connection. The Patient Server may process data received from one or more GPMDs (or a mixture of GPMDs and conventional non configurable devices) to filter, detect, and output clinically significant events from the sensed data, meaning that events that may be more difficult to detect within an individual sensors (or not possible at all) may be more easily identified.

The plurality of different medical devices may include at least a medical imaging device, such as an ultrasonic imaging device. Imaging sensors are connected via the patient sensor interface, and software functions are used to provide the imaging processing which may then be output to a display on the GPMD or may alternatively be communicated to a patient medical device controller (Patient Server/PPS) for further analysis/processing and/or displaying on a centralized display dedicated to the particular patient being monitored.

The patient medical device controller (Patient Server/PPS) may be configurable to retrieve the medical device data received, processed, and generated from a plurality of different programmable platform medical devices (GPMDs). Each of these GPMDs may be implementing a different medical device, some implementing more than one at the same time. The medical devices implemented by the GPMDs may comprise one or more devices selected from the group consisting of a Continuous Non-invasive tonometric-optical blood pressure monitoring (CNIBP) device, a 3-D topographic echocardiography device, an ECG device employing a 2D electrode array (to, for example, perform continuous vector imaging of the electrical activity of the heart), a 3-D vector ECG device and a 3-D Trans-Cranial Doppler device, for example. The medical imaging device may be configurable to perform substantially continuous patient imaging, in which case the image sensor(s) are preferably able to perform tracking of the target imaged region.

Thus, the patient data capture and processing system may further comprise at least one controllable device, coupled to the platform medical device, and the programmable platform medical device may then be controllable to adjust a resolution of an imaged region in one or both of space and time. The targeted image region may be selected under manual control via a user interface or more particularly either of both of the programmable platform medical device and the patient medical device controller may be configurable to automatically locate a target region of said patient for imaging. This may be achieved, for example, by employing the medical device controller to control the imaged region to target an organ or part of an organ in response to the detection of a clinically significant event, for example, a faulty heart valve.

Additionally or alternatively the system may include a controllable device for controlling administration of a substance such as a drug to a patient. The programmable platform medical device may provide the back end control/processing for a controllable device, again dependent on the functions and configuration of the GPMD, communicating with a mechanical front end use to provide the administration of the substance to the patient.

The patient data capture and processing system may further comprise a system server coupleable to said communications connection to store at least data representing clinically significant events. This may be useful to gather data for subsequent analysis, any may be used, for example, by a Patient Server to store or retrieve patient specific information.

Such a server (or a separate, dedicated server) may further be configured to store and authenticate software implementing the plurality of different medical devices on a plurality of said platform medical devices. In other words, the server may further act as an authentication server to control the implementation of different medical devices on the GPMD. This control/authentication may include permitted a change of implemented device or accessing new functionality, for example.

According to a second aspect of the invention there is provided a programmable platform medical device configurable to operate as a plurality of different medical devices, the platform medical device comprising: at least one patient sensor interface; and a processing module coupled to said sensor interface and coupleable to a function data store, said function data store configured to store one or more different patient sensing functions; wherein said processing module is configured to: retrieve a patient sensing function from the function data store to implement, in software, a medical device; receive sensor data from the at least one patient sensor interface; and process said sensor data responsive to said patient sensing function, wherein responsive to a device change request, the processing module is further configured to retrieve a further said patient sensing function to implement, in software, a different medical device.

In other words, the programmable platform medical device (general purpose medical device) is configurable to operate as a plurality of different medical devices. The change request may be one of a first request when the device is turned on to download an default configuration or a request to change function when a different form of sensing is required on a patient. A hospital may have sets of GPMDs allocated, for example, to each ward—when a particular medical device is needed, a GPMD can be retrieved, the particular medical device to implement selected, and the necessary functions downloaded from the function data store (which may be local or remote). Advantageously, this overcomes and limitation of limited device availability, allows for device upgrades, and provides for wider reuse of hardware. Moreover, compared to conventional dedicated devices, any specialized hardware that may be available for use in reduced quantities can instead be provided as a set of functions in the function data store, a GPMD accessing such functionality according to a physician's requirement.

Retrieving a further said patient sensing function may lead to the existing functionality being replaced, in other words, overwriting the existing functionality so that the GPMD takes on the function of a different medical device. Different sensors may need to be connected to the sensor interface in order for the device to function correctly, and/or sensor(s) repositioned on the patient. However, in some embodiments, the use of automatically adjustable sensors may overcome the need to reposition such sensors.

In variants however, retrieving a further said patient sensing function may lead to a different medical device being emulated in addition to the existing medical device being emulated so that, in effect, a combination of two medical devices is provided by the GPMD. This means that the GPMD may then take on the role of two conventional devices, subject to further sensors being connected to the GPMD to allow parallel operation. It will be appreciated that the capabilities to implement two or more devices at the same time may be dependent on the particular medical devices being implemented, the available resources on the GPMD (in particular in the processing module, but also on the sensor interface). The processing module may therefore use multi-core processing engines/CPUs, and/or programmable DSPs to provide the necessary processing resources.

In GPMDs (programmable platform medical devices) that have capabilities to implemented more than one medical device at the time, the retrieving of a further said patient sensing function may comprise replacing one or more of the currently implemented medical devices. One of the currently implemented devices, however, may be retained and may also continue to function whilst another is replaced.

As a security measure, the platform medical device may be configured to authenticate a device change request prior to retrieving further patient sensing functions to implement a different medical device. In other words, it is desirable to prevent any change in function without authorization to do so. Depending on the particular medical device being emulated, permissions may vary, even more so if a medical device is being emulated that controls delivery of a substance to a patient. Various authentication solutions are possible, including conventional numerical pin codes entry, individually allocated identification code, swipe cards, biometric authentication and the like. Authentication may be carried out by the GPMD itself, or may require use of a separate authentication server (which may optionally be incorporated into a Patient Server) in communication with the GPMD which centrally controls authentication and provides permissions to change functionality and implemented medical device on the platform. Authentication may also be function and/or implemented device specific. Furthermore, in variants, authentication may be needed to access stored functions. Authentication may further be necessary to access stored data, such as data stored on a patient either locally in the GPMD or remotely, such as in a Patient Server) to ensure such privacy of such data is maintained.

In some preferred embodiments the programmable platform medical device further comprises an analogue to digital conversion module configured to convert said sensor data to digital sensor data prior to said processing. However, in other variants, sensors may already include analogue to digital conversion and so it may be possible to provide lower cost GPMDs without any analogue interfacing/conversion.

The function data store may be provided within the programmable platform medical device (GPMD). Stored locally, this may provide a library of different sensing functions to implement, some of which may be reused across different implemented medical devices, others of which may be implemented device specific. Multiple functions may needed to be accessed in order to implement a medical device. Local storage may be in flash memory, hard disk, or any other conventional forms of storage. The GPMD may also provide a memory card reader and/or USB interface (or the like) and the functions (functions for implementing a medical device) provided on a memory card or USB memory drive, for example.

A local function data store may also provide a temporary cache of most frequently used functions for implementing devices, the GPMD accessing a separate function data store (connected across a network for example) to obtain further functions. The patient medical device controller (Patient Server) may also provide the function data store, with the GPMD communicating with a patient medical device controller to retrieve further sensing functions.

The processing module may be further configured to retrieve a controlling function from the function data store for controlling administration of a substance to a patient so that effector devices may further be implemented. Thus, the GPMD may then perform a controlling function and output control data for controlling at least one controllable device (effector device). This may be, for example, to deliver a substance to a patient responsive to the controlling function. A GPMD implementing a controlling function may also be under the control of a Patient Server for example, which has received data from one or more other GPMDs implementing sensing medical devices, assessed the necessary operation to perform, which may then be communicated to a connected GPMD delivering the substance to a patient in response to the previously sensed and analysed data.

The processing module in the programmable platform medical device may be configured to identify a sensor connected to the at least one patient sensor interface, meaning that no manual configuration is required. This may however rely on device specific sensors being connected to the GPMD. In response to such automatic detection, the GPMD may then bay able to automatically retrieve the appropriate patient sensing functions dependent on said identified sensor, meaning that the GPMD may be able to be rapidly configured and available for prompt use.

A real-time operating system may run in the processing module. This may be necessary when a GPMD is configurable to implement multiple medical devices at the same time to ensure that any mandated hard real time constraints are maintained.

The programmable platform medical device may preferably be fail safe (failing to safe state) or fault tolerant (being able to tolerate at least one fault) depending on the criticality of the implemented medical device. Any spare processing resource may optionally be used to provide further checking of data and actions; a real-time operating system may provide further safety features such as watchdog timers for example.

Examples of the plurality of different medical devices that may be implemented include a medical imaging device, such as an ultrasonic imaging device. Other examples of the plurality of medical devices comprises one or more devices selected from the group consisting of a Continuous Non-invasive tonometric-optical blood pressure monitoring (CNIBP) device, a 3-D topographic echocardiography device, a 3-D vector ECG device and a 3-D Trans-Cranial Doppler device. Another example is an infusion pump.

The programmable platform medical device may further be configured to control the positioning of an adjustable sensor coupleable to the patient sensor interface, meaning that it can provide any necessary adjustments in order to optimize the sensing. To enable continuous patient imaging using the adjustable sensor, the function data store may comprise code to perform substantially continuous patient imaging using the adjustable sensor coupleable to the patient sensor interface.

According to a further aspect of the invention there is provided a programmable platform medical device configurable to operate as a plurality of different medical devices, the platform medical device comprising: at least one patient effector interface; and a processing module coupled to said effector interface and coupleable to a function data store, said function data store configured to store one or more different controlling functions; wherein said processing module is configured to: retrieve a controlling function from the function data store to implement, in software, a medical device; perform said controlling function, and output control data to the patient effector interface for controlling at least one controllable device, said controllable device arranged to deliver said substance to said patient responsive to said performing said controlling function; and wherein responsive to a device change request, the processing module is further configured to retrieve a further said controlling function to implement a different medical device.

It will also be appreciated that the programmable platform medical device may interchangeably function as a plurality of different medical devices, changing from sensing functions to control functions and vice versa. In embodiments, the programmable platform medical device may also function as a sensing device and controlling device at the same time.

Features from the above described aspects and embodiments of the invention may be combined in different permutations.

BRIEF DESCRIPTION OF DRAWINGS

These and other aspects of the invention will now be described, by way of example only, with reference to the following drawings in which.

DETAILED DESCRIPTION OF THE PREFERRED EMBODIMENTS

Patient Server/Medical Console

Figure 1A:
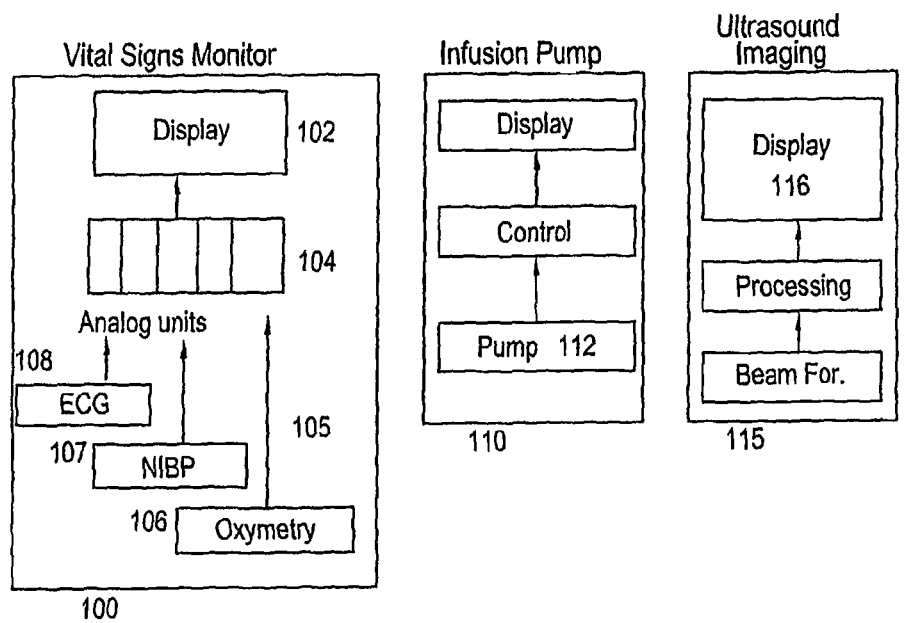
FIG. 1a shows an example of the prior art with each medical device working independently.
Figure 1B:
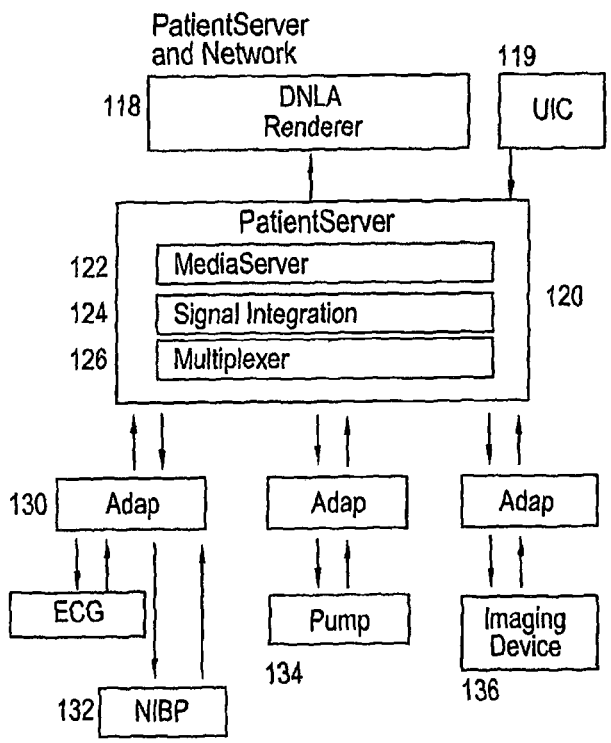
FIG. 1b shows an overview of the medical console (Patient Server) as provided in British Patent Application No. GB1120345.2 in which device monitoring and medical devices for drug delivery are combined.

Today medical devices are dedicated independent devices and there is an urgent unmet need for a unified platform that will make drastic cost reduction in devices' cost and cost of clinical and administration as well as enable easy and frequent upgrades and selling additional new features (similar to the S/W industry). This can be achieved with a Personal Patient Server (Patient Server/Medical Console/PPS), General Purpose Medical Device (GPMD) and Automatically Adjustable Sensors (AAS):

PPS—attached to the patient and acts as an "Active Patient Chart" in actively controlling all medical devices around the patient and connection to the hospital server/cloud. The PPS also does the culling of huge amount of data and detects and transfer only clinical significant events.

GPMD—Provides a programmable platform medical device that is software configurable to provide a range of medical devices, including 3-D Tomograpic imaging to continuous monitoring of Blood Pressure, ECG, Arterial Blood gases, etc.

AAS—Automatically adjustable sensors & effectors that automate placement and tracking of sensors and actuators.

Also developed are new devices for Continuous Non-Invasive BP monitoring (CNIBP), Improved Oxymetry and perfusion continuous monitoring, Vector ECG, 3-D ultrasonic tomography, online Arterial Blood Gases, Blood PTT, Glucose, Hemoglobin, etc.

We refer herein to a Patient Server/Medical Console, which is described in detail in related application patent application GB1120345.2.

The Patient Server as herein summarised is an active patient-chart that accompanies the patient, actively collecting relevant clinical information from a plurality of medical devices around the patient. The Patient Server may accompany a patient from admission to release, acting as an "Active Patient Chart".

The Patient Server also analyzes the patient's health state by combining all the information as well as applying effectors to interrogate and treat the patient based on that information. In many examples of the system such control may also be under the caregiver control.

The Patient Server is able to collect information relevant to a patient state (from the sensors for example) in real-time, performs real time analysis of the patient's health state and applies the necessary effectors both to interrogate and treat the patient with the intention of bringing the patient into an improved health state. Such a device may also be under the care giver control.

As an "Active Patient Chart", the Patient Server may combine and record continuously and in real time all the data relevant to the patient clinical status. This is different to current systems where, for example, a regular infusion pump is not "aware" what drugs it delivers. In the present invention, the Patient Server is fed with the pharmaceutical information of the injected drugs, so it may cross correlate the expected effect with the physiological change, as measured by the vital signs and other sensors.

Signal combination in the Patient Server can be used to generate additional signals that are not measured directly (e.g. generating central blood pressure signal from peripheral signals). Combination of signals can be used also to create discrete and continuous new parameters and signals such as Cardiac Output. Moreover, any transformation of signals, such as the computation of Cardiac Output from BP waveform may result in a reduction of signal to noise ratio in the signal. This can render the transformation of little or no clinical value and make it prone to critical mistakes in estimation. By combining signals, these limitations may be overcome.

The medical console (Patient Server/PPS) provides a central resource for managing the care of a patient and as such, may be positioned at a patient's bedside or remotely controlled. One or more sensors are connected to the medical console as well as one or more effective devices (which may be, for example a treatment device used to treat a patient. In the medical console, an analysis engine processes the sensor data received from one or more sensor devices and can generate control data used to control an effector device in response to the sensor data. The analysis engine determines a divergence of the sensor data to a target health state for the patient and then generates the control data for outputting to one or more effector devices in response to this determined divergence. A target health state (a predetermined clinical goal) may comprise one or more different characteristics which may be derived from stored data relating to the patient, data derived from learning an anticipated response to the particular sensor data readings, from predetermined or pre-programmed information configured by for example a medical practitioner. It may be, for example, an intention of keeping the heart rate within a predefined range, or a number of activations of a ventilator per minute. Further ways of determining the clinical goal may also be possible. Moreover, such a divergence may vary depending on the condition of a patient and so such data may vary over time. An effector device, for example a treatment device, can then receive such control data from the medical console and control the operation of the device accordingly so that it may counteract any change in condition (or maintain the existing condition). The personal medical console may also be adapted for use by a medical professional at a patient's bedside.

The General Purpose Medical Device (GPMD)

In the future, the role of imaging and especially ultrasonic imaging will become dominant and will replace the stethoscope of today. The GPMD may emulate a device as sophisticated as ultrasound imaging with sufficient processing power. It may also emulate one or more simple devices like BP monitors, or even extend the number of leads in ECG beyond the twelve leads used today to get a 3-D electrical imaging of the heart.

Existing medical devices are often hard-wired to measure or monitor a specific parameter or set of parameters. In existing devices sensors are typically also an integral part of the device and are positioned by a caregiver or by the patient at home.

By contrast, the GPMD described herein can be used to provide the processing/analysis functionality of one or more medical devices. Sensors and effectors can also be controlled to change position, orientation and function under control of the GPMD. The functionality of the GPMD depends on the choice of sensors and effectors and the configuration of the GPMD itself (typically controlled by uploaded a software application/configuration).

We describe a general purpose medical device (GPMD) suitable for sensing and/or use as a treatment device whereby the device functionality is determined by the software configuration. Thus, the GPMD provides a programmable platform for providing one or more medical devices, both simultaneously (subject to resources) and/or by being reprogrammable to change functionality and emulate different devices.

Such programmable general purpose devices, with preferably adjustable sensors and/or effectors, can be part of a Patient Server network described in related application patent application GB1120345.2 (and described herein) or stand alone. When used in conjunction with the Patient Server, the GPMD may be used as a medical device in the Patient Server network for combining measurements, monitoring, imaging, clinical data including models and effectors for a patient.

The GPMD may be provided with, for example, the analogue abilities needed to interface with sensors, the motor control abilities needed to interface with effectors, and the Biological Signal Processing libraries needed to implement on it a wide range of medical devices by uploading an application and connecting the sensors and effectors. Such libraries may incorporate information allowing for automatic adjusting of one or more involved parameters, including 3-D positioning, intensity of interrogation, depth levels, pressure etc.

The GPMD may be used as, for example, a monitoring device, a medical imaging and drug delivery device (e.g., infusion pump), an effector device with interrogation capabilities and/or treatment capabilities (for example, in Continuous Non-Invasive Blood pressure monitoring, an effector device may change the pressure level of the sensor.)

The GPMD may provide the back-end compute/processing functionality for sensor devices and effector devices, meaning that front-end sensors, used for providing an input to various monitoring devices such as ECG, PPG, Blood pressure and the like are attached to a patient are then connected directly to a GPMD rather than a device specifically designed to process the sensor data and provide, for example, the ECG, PPG, or blood pressure information. This is different to conventional dedicated devices. Examples of effector devices include infusion pumps, ventilators. The GPMD may also provide the back-end processing functionality need to operate and control the analogue/mechanical delivery front-end of such effector devices.

The GPMD, capable of providing one or more medical devices, may be controlled by the Patient Server (medical console).

Whilst the Patient Server may typically accompany a patient from admission to release, acting as an "Active Patient Chart", the GPMDs, in a hospital environment may typically belonging to a room or a ward, being configured to act as a specific device dependent on the requirements of each patient. In a variant however, GPMDs may be incorporated into the same platform as a Patient Server, with both provided as part of the same unit. In the latter configuration, further GPMDs may also be connected to the Patient Server if further devices are required.

Figure 1C:
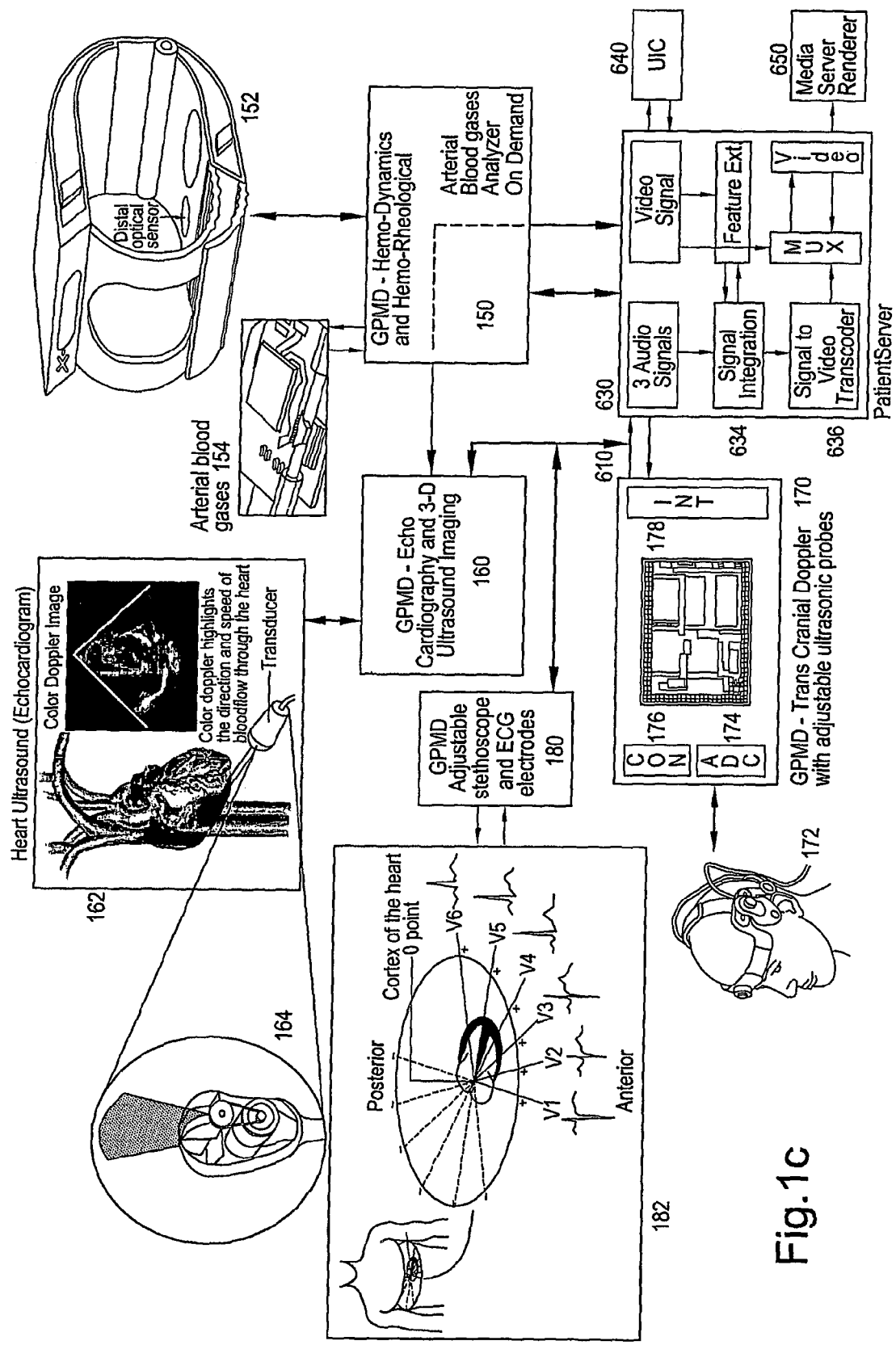
FIG. 1c—Depicts the schematic structure of a Patient-Server 630 connected to four General Purpose Medical Servers, where each of them is connected to adjustable sensors and effectors.

The sensors and effectors may also include, in addition to the sensor and effectors themselves, the electronics to enable them to function under control of the GPMD. For example, if, as is shown in FIG. 1c, a 3-D mechanical scanning ultrasound probe 164 is used, the combination of piezo-array sensor and the motor effector may include the analogue power circuit for driving the scanning motor. As another example, in Transducer Electronic Data Sheets (TEDS) sensors, functionality is included in the sensor to store its ID and features to make it "Plug & Play".

By using GPMDs instead of the existing dedicated medical devices each having different interface, all devices are provided by a uniform hardware structure and their functionality can be enabled and updated as needed by uploading the software, including applications and libraries to the GPMD—i.e. the GPMD provides a standard platform for device provisioning. This leads to a reduction in cost for hospitals adopting such devices as instead of buying great number of devices that are used only small fraction of the time, functionality can be changed according to the needs in any moment and for any patient. This makes maintenance much simpler and allows continuous updating and adding features through the use of software updates. Furthermore, existing devices may even be retrofitted with a new GPMD "heart" and become a GPMD. Many medical devices include a processor and analogue front-end and so may be retrofitted by replacing its processor and software (including the Operating system), and use part of its analogue circuitry without changing the housing. Since the functionality does not change, this may save efforts on obtaining regulatory clearance (CE mark/FDA pre-market clearance and the like).

The use of sensors, in particular automatically adjustable sensors (AAS) and effectors, the use of one or more GPMDs and the PatientServer leads to the following arrangement of devices:

Patient→Sensors & effectors→GPMDs→PPS→Caregiver (e.g., doctor/nurse)

In this arrangement the GPMDs are positioned between the front-end analogue sensing capabilities of sensors/analogue front-end delivery of effectors and the digital Patient Server. The Patient Server manages the devices; the GPMD, acting as a sensor device for example takes the sensor data from the sensor and provides a the back-end processing to provide a functional sensor device.

The GPMD includes analogue conversion, including, for example, A-to-D converters and D-to-A converters/PWMs to interface with sensors and effectors.

The General Purpose Medical Device (GPMD) includes biological signal processing libraries that enable it to emulate a very wide range of devices, from sophisticated medical imaging to simple devices like BP monitor or an infusion pump.

FIG. 1c presents four GPMDs 150, 160, 170 and 180, that can use multitude adjustable sensors and multitude adjustable effectors that can measure and monitor many different parameters depending on the implemented functionality.

Adjustable positioning of sensors and effectors is also possible. Today the sensors and effectors are normally positioned by a healthcare giver and their placement and positioning can be changed only manually by the care giver.

In many cases, this requires special skills and expensive time and resources that also limit the situations where such placement can be made.

An example of an adjustable wrist assembly 152 that includes pressure sensor and optical sensor are shown for the GPMD 150 that functions as a Continuous Non-Invasive hemodynamic and hemo-rheological monitor. There is a more detailed explanation given with reference to FIG. 2a.

An example of an adjustable ultrasonic imaging sensor 162 and 3-D scanning effector 164 are shown for the GPMD 160 that functions as a Continuous Non-Invasive Cardiac Output and Left Ventricle volume estimator.

An example of an adjustable ultrasound sensor 172 is shown for the GPMD 170 that functions as a Continuous Non-Invasive blood flow device using a Doppler ultrasonic technology to estimate the blood flow in a desired artery. More details on this adjustable sensor are provided below in the explanation of FIG. 3.

An example of adjustable Stethoscope and ECG electrodes sensors 182 for recording lungs and heart sounds and composing a 3-D vector-cardiogram from V1 to V6 leads ECG are shown for the GPMD 180 with real time chest auscultation and ECG multi-lead functionality.

Figure 2A:
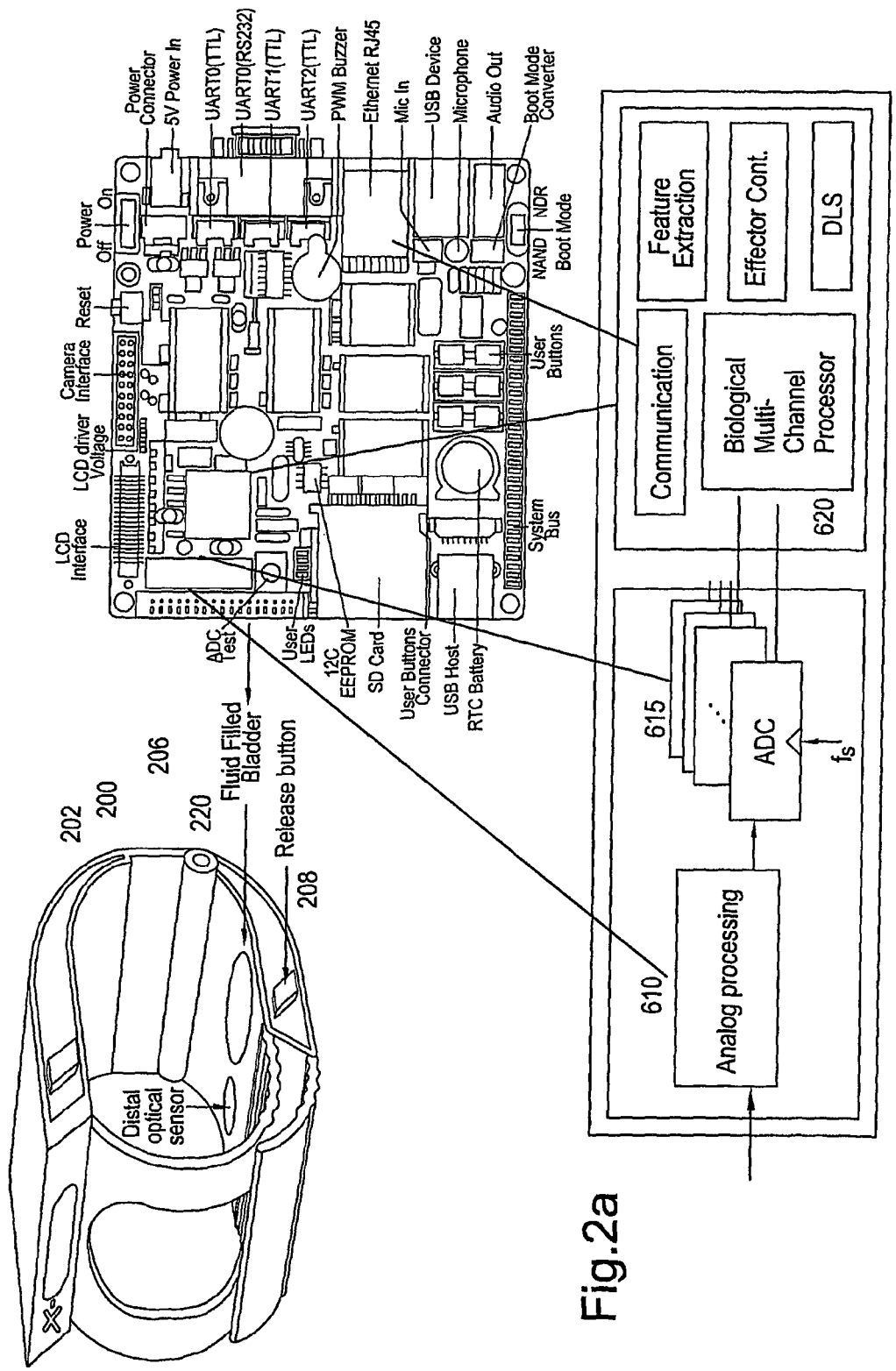
FIG. 2a shows further details of the adjustable sensors and effectors in the wrist assembly for measuring hemodynamic and hemo-rheological parameters.
Figure 2B:
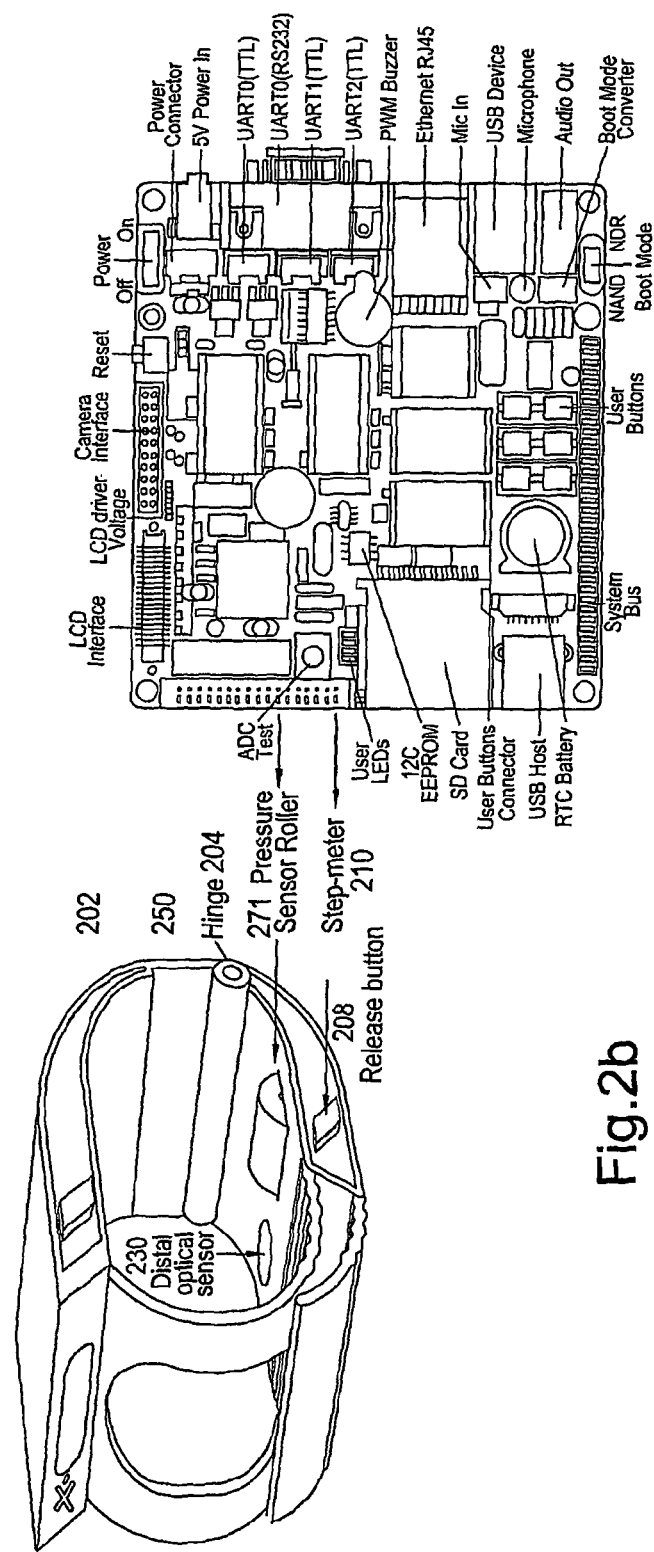
FIG. 2b shows further details of another embodiment of the adjustable sensors and effectors in the wrist assembly for measuring hemodynamic and hemo-rheological parameters.
Figure 2C:
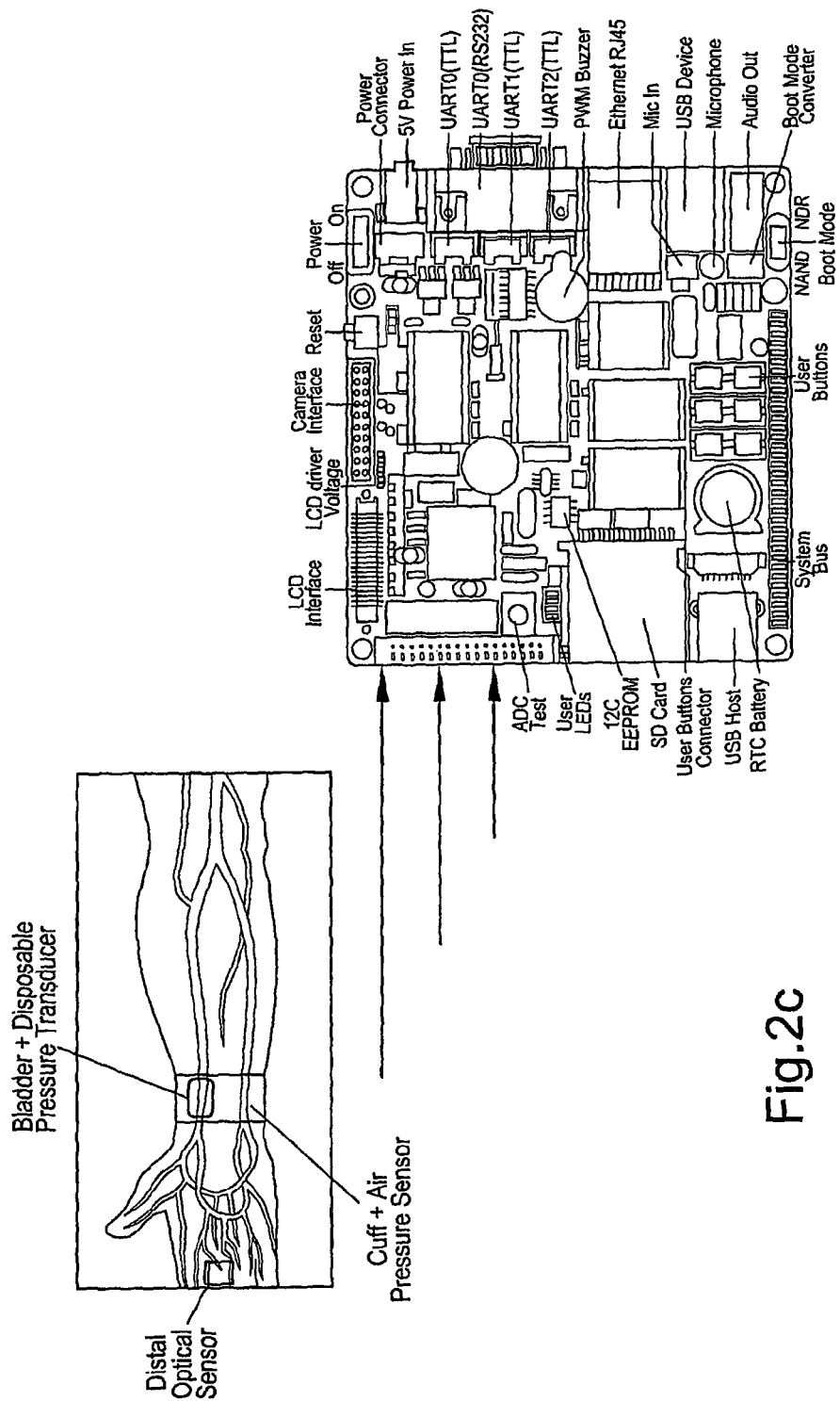
FIG. 2c shows another embodiment of the adjustable sensors and effectors in the wrist assembly using mini-cuff to adjust hold-down force and finger distal optical sensor for measuring hemodynamic and hemo-rheological parameters.

FIGS. 2a and 2b describe automatically adjustable sensors and effectors wrist assembly that is part of medical devices that can measure hemo-dynamic and hemo-rheological parameters, based on the software uploaded to it. These sensors and effectors are controlled by a GMPD depicted next to them.

FIG. 2a depicts combining a Continuous Non-Invasive BP pressure sensor 270 and a distal optical sensor 230. The BP sensor 270 can be either a single sensor or two sensors, one on top of the other with an elastic member between them. Optical sensor 230 may be either a DLS (Dynamic Light Scattering) type or other optical sensor positioned distal to the pressure sensor 270 but on the same Radial artery for computing Hemodynamic and Hemo Rheological data. Both sensors 270 and 230 are self positioning in this example. They use effectors 206 and 210 (such as a spring or step motor) to position the sensor and apply pressure through roller 230.

One example of Hemodynamic parameters is Continuous Cardiac Output monitoring. One way to compute cardiac output is to calculate it from the Arterial Pressure Cardiac Output (APCO). For that, there is a need for a continuous BP signal as the cardiac output is computed from the stroke volume that is estimated from the area under the incident component of the BP wave form, multiplied by the heart rate. The BP signal can come from an invasive Arterial Line, or non-invasively from a tonometric device. In this case we can use wrist holder like the ones depicted in 2a or 2b that has 1 or 2 sensors and one effector.

The wrist device has a distal optical sensor and proximal force sensor or force/pressure sensing. In the first preferred embodiment (FIG. 2a) the proximal force sensor is a fluid filled bladder 220 that communicates with a pressure transducer (not shown in the fig.). In a second preferred embodiment, the sensor or sensors are connected mechanically to a roller 230 that can move laterally across the Radial artery in order to position itself above the Radial artery. Both bladder 220 and roller 230 sensors can be pressed against the artery by an inflated bladder under the fluid filled bladder 220 or a step motor 210 that tightens or relieves the hold-down force.

All this can be controlled by a local controller of the GPMD but will be under the overall control of the Patient-Server in a configuration where the PatientServer is employed. In such case the doctor can control all GPMDs through the Medical Console or the PatientServer that can override the local controller commands.

This is very different from the existing BP devices. In these devices, the local controller provides an On-Off command to a pump and the pressure sensor is sensing the BP pulse amplitude in a predetermined pressure decay curve. Positioning of the sensor is conventionally done manually by the care giver.

In the present invention, the roller 270 can be rolled in the lateral direction of the arm, across the Radial artery (rolling effector). The reasons for using a cylindrical shape roller are to minimize friction with the skin but also to keep the sensor (that is connected to the roller axis) always perpendicular to the compressed artery. Then the GPMD can position the roller 270 above the Radial artery and correct positioning if the sensor moves during the monitoring. The GPMD can also change the hold-down force to reach the desired pressure and release this hold-down force when needed. The GPMD can use also the distal optical sensor signal to determine the optimal positioning of the roller, as well as determine more accurately Systolic and diastolic points.

The wrist device in FIG. 2a is made to enable easy and fast placement. The caregiver or patient presses the green button 208 that releases the ratchet of the belt, then pushes their hand through it. The belt will extend as much as needed and the sliding ratchet 202 will extend the C clamp to accommodate the wrist size of the patient. The step motor in 206 will make the lower part of the C-Clamp with the roller slide out until the roller starts to sense the arterial pulse. The optimal point will be computed by the GPMD software application for continuous BP according to the Pulse wave shape. In some preferred embodiment the distal Optical sensor can assist as it is positioned along the same line of the Radial artery.

The roller can be pressed against the artery and the hold-down force is controlled by the GPMD.

Figure 3:
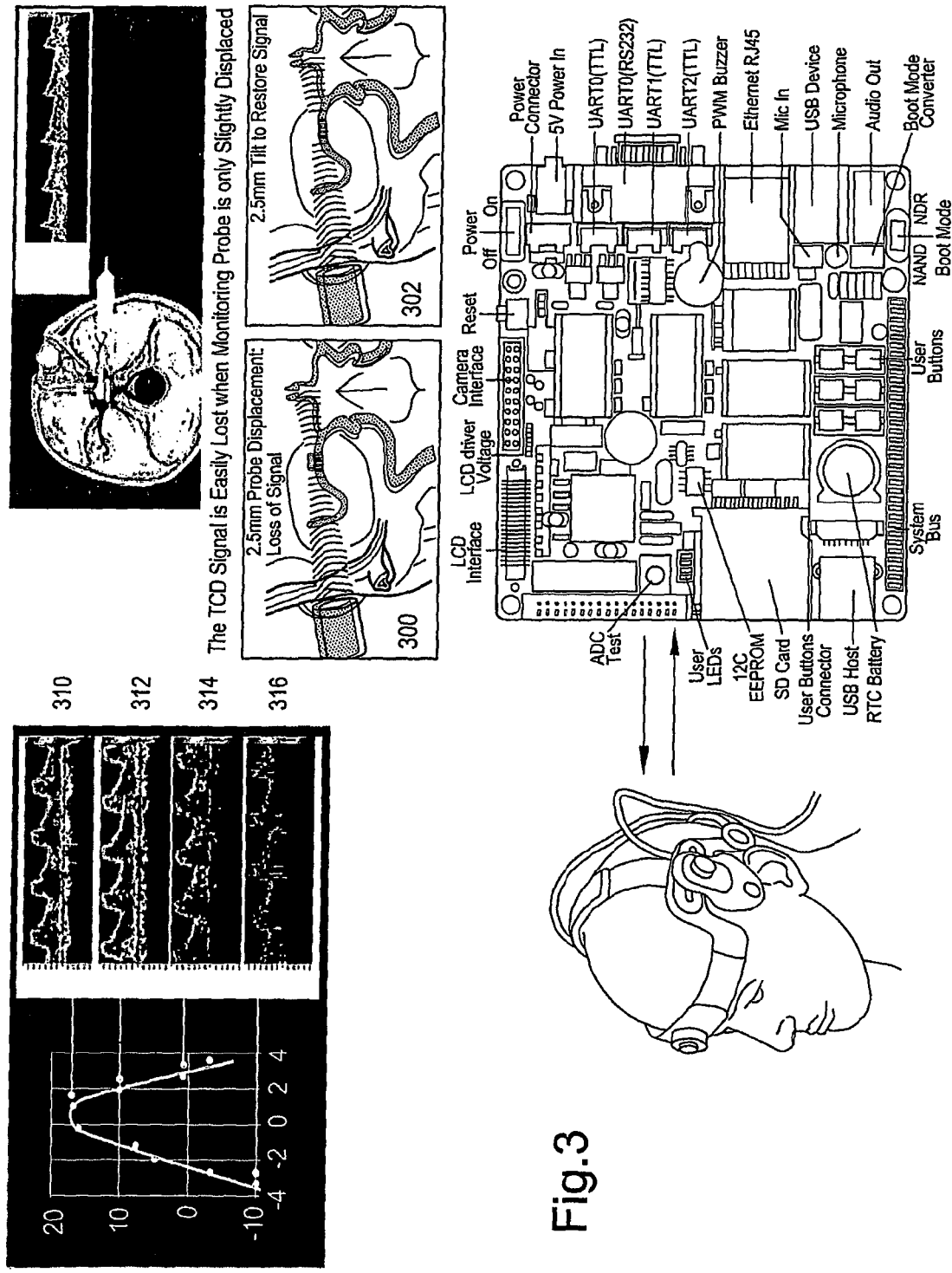
FIG. 3 shows further details of the adjustable sensors and effectors in the a headgear Trans Cranial Doppler ultrasound.

FIG. 3 depicts an automatically adjustable ultrasonic probe in a Trans Cranial Device (TCD) application. The placement of Trans Cranial Doppler (TCD) ultrasonic sensors require special skills of the doctor to find the correct positioning and placement, thus limiting this useful technology to situation where such experienced doctors are available. TCD can help in determining if a stroke has been caused by locking of a brain blood vessel by a thrombus, or if it caused by internal haemorrhage. The treatment is completely different. In a stroke that is caused by a thrombus blocking a brain artery, the treatment is by anti-coagulants and thrombus dissolving agents. However, if the stroke is due to arterial haemorrhage, the treatment should stop the haemorrhage and any anti-coagulation medicine may just exacerbate the patient's haemorrhage—i.e., misdiagnosis can aggravate the patient's condition by delivering anti-coagulants to a hemorrhagic stroke. A TCD device however needs expertise in placing the sensors and cannot be operated when it is needed most—in the patient's home or in an ambulance where a doctor skilled in positioning TCD is unlikely to be present.

Therefore, an adjustable position, orientation and function sensor that can be controlled by the software application can save a lot of lives in such emergency cases, where each moment is critical.

A similar idea can be used also for an ultrasound probe that can change position (by rolling or panning or tilting) under the GPMD control. The idea of combining BP sensing and Echocardiography is shown in FIG. 3. In this example the probe changes position under control of the GPMD that emulates both a 3-D ultrasonic tomographic imaging and Continuous Non-Invasive BP.

Then, by combining the signals from the Force sensor, Optical sensor, and Ultrasound imaging the PatientServer can compute the Cardiac Output in great accuracy. The 3 effectors (2 rolling and one hold down force) and 3 sensors (roller force sensor, distal optical sensor and ultrasound sensor) have to work in concert and can be adjusted in real-time under the PatientServer control.

Figure 4:
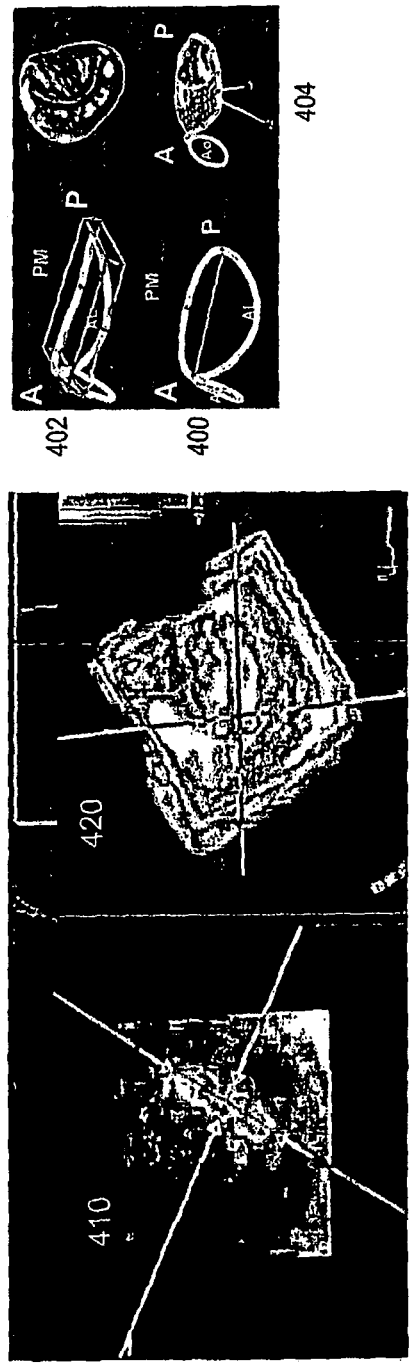
FIG. 4 shows further details of the adjustable sensors and effectors in the a Echocardiography with ability to extract surgical view of a mitral valve from volume voxels data and monitor continuously the Cardiac output and other cardiac parameter.
Figure 4:
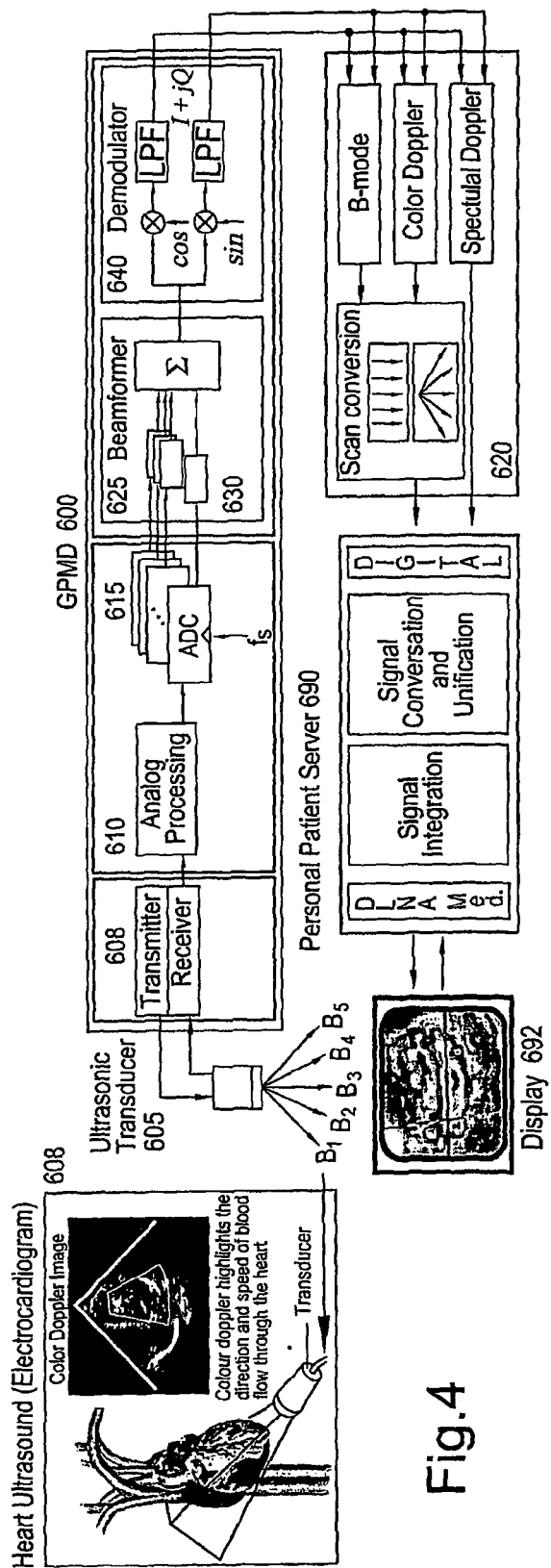

FIG. 4 shows further details of the adjustable sensors and effectors in use for Echocardiography, with ability to monitor continuously the Cardiac output and other cardiac parameters.

The adjustable sensor can be both positioned and adjusted before the actual measurement, or acquiring big volume of data and do the adjustment and selection after capturing, to extract the needed info or view. In this example we show how from a big volume of voxels generated by the pyramidal volume produced by 3D ultrasonic sensor 605, we can select a specific measurement that we are interested in. The colour Doppler that provides blood flow velocities data as depicted in 608, enables us to measure flow like the vena contracta for the mitral valve.

One of the major issues in 2D ultrasound imaging is that it requires special skills and knowledge from the radiologist and, therefore, limits its use to the few doctors that can do this analysis. Even for them, there is a lack of objective measure for parameters of a 3D structure like the mitral valve shown below in 400, 4002, and 406. Also for the surgeon that is going to operate on the mitral valve, we need to reconstruct a "surgical view"—an en-face view similar to what the surgeon is used to seeing during surgery.

In our example depicted in FIG. 4, we demonstrate extracting from the pyramidal volume of 3D Echocardiograpy generated by 605 sensor, the size of the vena contracta of blood flow through the mitral valve and presenting a surgical view of the Mitral valve. Multiple-beat 3D echocardiography provides images of higher temporal resolution. This is achieved through multiple acquisitions of narrow volumes of data over several heartbeats (ranging from two to seven cardiac cycles) that are subsequently stitched together to create a single volumetric data set. However, gated imaging of the heart is inherently prone to imaging artefacts created by patient or respiratory motion or irregular cardiac rhythms.

Simultaneous multi-plane imaging is unique to 3D Echography (3DE) by a mechanical scanner or a 2D matrix array transducer and permits the use of Full Volume-Gated Acquisition. The full volume mode has the largest acquisition sector possible, which is ideal when imaging specific structures such as the mitral valve or aortic root. This mode also has optimal spatial resolution, which permits detailed diagnosis of complex pathologies. As well, it has high temporal resolution (>30 Hz). This high resolution large volume enables the S/W to compute complex structures like the mitral valve shown in FIG. 4 and designated as 400, 402 and 404 in different stages of the calculation.

The gated full volume can also be rotated to orient structures such as valves in unique en face views 420 (Also presented on the display 692).

Furthermore, the full volume data set can be cropped or multiplane transected to remove tissue planes in order to identify components of valvular structures within the volume or to visualize 2D cross-sectional x, y, and orthogonal planes using off-line analysis software.

The main trade-off in 3DE imaging is between Temporal Versus (or volume rate) and Spatial Resolution. To improve spatial resolution, an increased number of scan lines per volume (scan line density) is required, which takes longer to acquire and process and thereby limits the overall volume rate. Fortunately, imaging volumes can be adjusted in size to increase volume rate while maintaining spatial resolution. Because of the frequent artifacts associated with gating, ultrasound companies are developing real-time technology associated with methods for improving the ultrasound system processing power needed to provide full volume (90) real-time 3DE data sets with adequate spatial and temporal resolution. The advantage of a GPMD is that the processing power and volume rate can be updated frequently by adding processing modules and adjusting the spec to the needed resolution. It does not require any training or special skills from the care giver that should just ask for mitral valve surgical view, including the vena contracta.

Gated data sets may be challenging in patients with arrhythmias and/or respiratory difficulties. The concept of cropping is inherent to 3D echocardiography and is essential; to our concept adjustable sensors by selection. In contrast to cross-sectional (i.e., tomographic) modalities, 3D echocardiography requires that the "viewing perspective" be in the chamber that is in immediate continuity with the region of interest. For example, to view the atrioventricular junctions "en face," the operator must crop off the base and the apex of the heart, so that the operator may visualize the junctions looking up from below, or looking down from above. Similarly, to view the ventricular septum en face, the echocardiographer must crop off the free walls of both ventricles to view the right ventricular (RV) aspect of the septum from right to left or the LV aspect of the septum from left to right. The paradigm for the AAS in our case is to enable the surgeon to change from the cross-sectional approach in 2D ecocardiograpy (like in 608) to that of the surgeon like we display in 692, that is, viewing intracardiac structures after exposing them, by selection or cropping the walls of the different chambers. Three-dimensional cropping can be performed either before (during) or after data acquisition. In a GPMD that its S/W is built for that, we can save a lot of un-necessary processing by doing the cropping during the data acquisition.

Cropping that is performed before the acquisition has the advantages of providing better temporal and spatial resolution, while also providing immediate availability of the cropped image. However, if a cropped image is stored, that image may not be amenable to "uncropping" later. In contrast, if a wide data set is acquired and cropped after acquisition, it provides the advantage of retaining more diagnostic information, but at the expense of loss of spatial and temporal resolution. In our GPMD approach, we can upload the S/W application to meet the surgeon's choice.

Volumetric quantification of the mitral valve as shown in 402 allows accurate measurements of the height of the saddle-shaped mitral valve 402, commissure-to-commissure diameter measurements of the mitral annulus 400, mitral annular surface area 406, and the angle between the aortic root and the mitral annulus 404. In this sub figure of FIG. 4 on the top right: A—Anterior; AL—anterolateral; Ao—aorta; P—posterior; PM—posteromedial.

Figure 5:
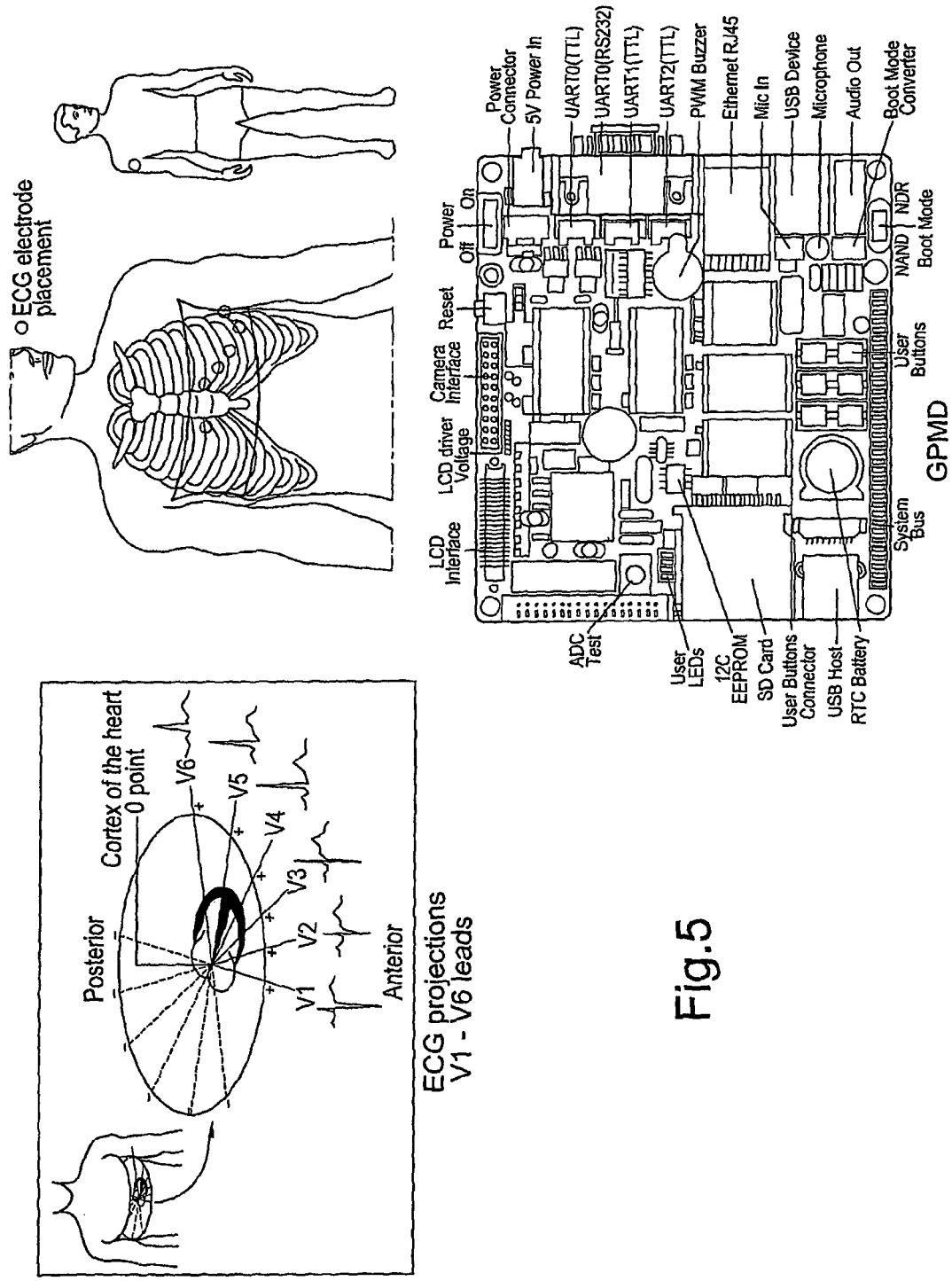
FIG. 5 shows further details of the adjustable sensors and effectors in the a chest harness that can contain both stethoscope microphone for phonocardiography, ultrasonic probe and/or ECG electrodes.

FIG. 5 shows further details of the adjustable sensors and effectors in a chest harness that can contain both stethoscope microphone for phonocardiography, ultrasonic probe and/or ECG electrodes.

A twelve Lead ECG can be used for computing Vector-Cardio-Graphy (VCG), which is more informative than ECG on cardiac ischemia. Knowledge of the location and size of ischemic myocardium at risk for infarction could impact pre-hospital and hospital patient triage and reperfusion therapy. The twelve-lead electrocardiogram (ECG) can roughly estimate ischemia size; however, individual precordial ECG leads are at different distances from the left ventricle (LV) and certain LV walls have greater effects on the ECG. The use of a 2-D array of electrodes as shown in FIG. 5 can make this estimation far more accurate and informative, including a 4-D VCG (3-D VCG over the 4th dimension of time. Vector-Cardio-Graphic corrected orthogonal lead systems can display the magnitude and direction of the ST-segment "injury current" vector in 3-dimensional space. What we suggest is a 2D (matrix) electrode array based vectorcardiographic ST-vector direction and magnitude derived from the ECG by the inverse-Dower method to estimate the location and size of ischemia. To put in context, traditional ECG is based on a limited number of electrodes—typically six on the chest (V1-V6) and four electrodes on the four limbs. Each electrode enables viewing of the heart dipole from a different angle, thus produces a different wave form. It can be tricky and time consuming, requiring skill, to place the V1-V6 electrodes in specific positions on the chest (e.g. V1 has to be placed right next to the sternum, between ribs 4 and 5). If electrodes are not placed correctly, there is no way to compare ECG traces taken with different positioning. To automate this process, the electrode array harness provides almost continuous change in viewing angle and thus a much more complete and repeatable true reflection of the 3D electrical field generated by the heart.

It has been shown (J Electrocardiol. 2009 March-April; 42(2): 190-7.Vectorcardiogram synthesized from the 12-lead electrocardiogram to image ischemia. Strauss D G, Olson C W, Wu K C, Heiberg E, Persson E, Selvester R H, Pahlm O, Arheden H. Department of Clinical Physiology, Lund University Hospital, Lund, Sweden.) that the ST-vector direction derived from the inverse-Dower method can be projected to an LV model with normal coronary artery anatomy. The graphical display of ST-vector location could discriminate among occlusions of the different coronaries. ST-vector magnitude had been shown to have a statistically significant correlation with SPECT (single photon emission computed tomography) ischemia size.

The 3-dimensional ST vector derived from the ECG can be graphically projected onto an LV model to localize ischemia, and ST-vector magnitude correlates with ischemia size. This VCG imaging can risk-stratify and provide decision-support for patients with acute myocardial infarction.

The same GPMD may function as BP monitor, Ultrasound imaging or Infusion pump, the GPMD providing both software and processing hardware to provide these in addition to mechanical pumps/sensors and the like. As the GPMD has a real time Operating System that can deal with multitasking, it can implement more than one device at the same time and expose to the Personal PatientServer, two or more devices simultaneously.

It will be appreciated that there is a distinction between monitoring, which comprises continuous measurement and displaying (E.g. ECG, Continuous invasive BP, PPG, Respiration etc.) and imaging (Ultrasound, MRI, CT, X-Ray and the like) that are performed once. Automatically Adjustable Sensors are particularly useful for continuous imaging (continuous patient imaging) that cannot be performed unless the sensors are able to provide continuous tracking. As an example, to monitor a specific heart valve, the 3D ultrasound sensor (probe) may start with a wide angle and wide range gate scanning to locate the target heart valve, and then narrow down the scanning beam and narrow the range between the range gates (under GPMD control) to gain higher resolution (both spatial and time resolution).

Figure 6:
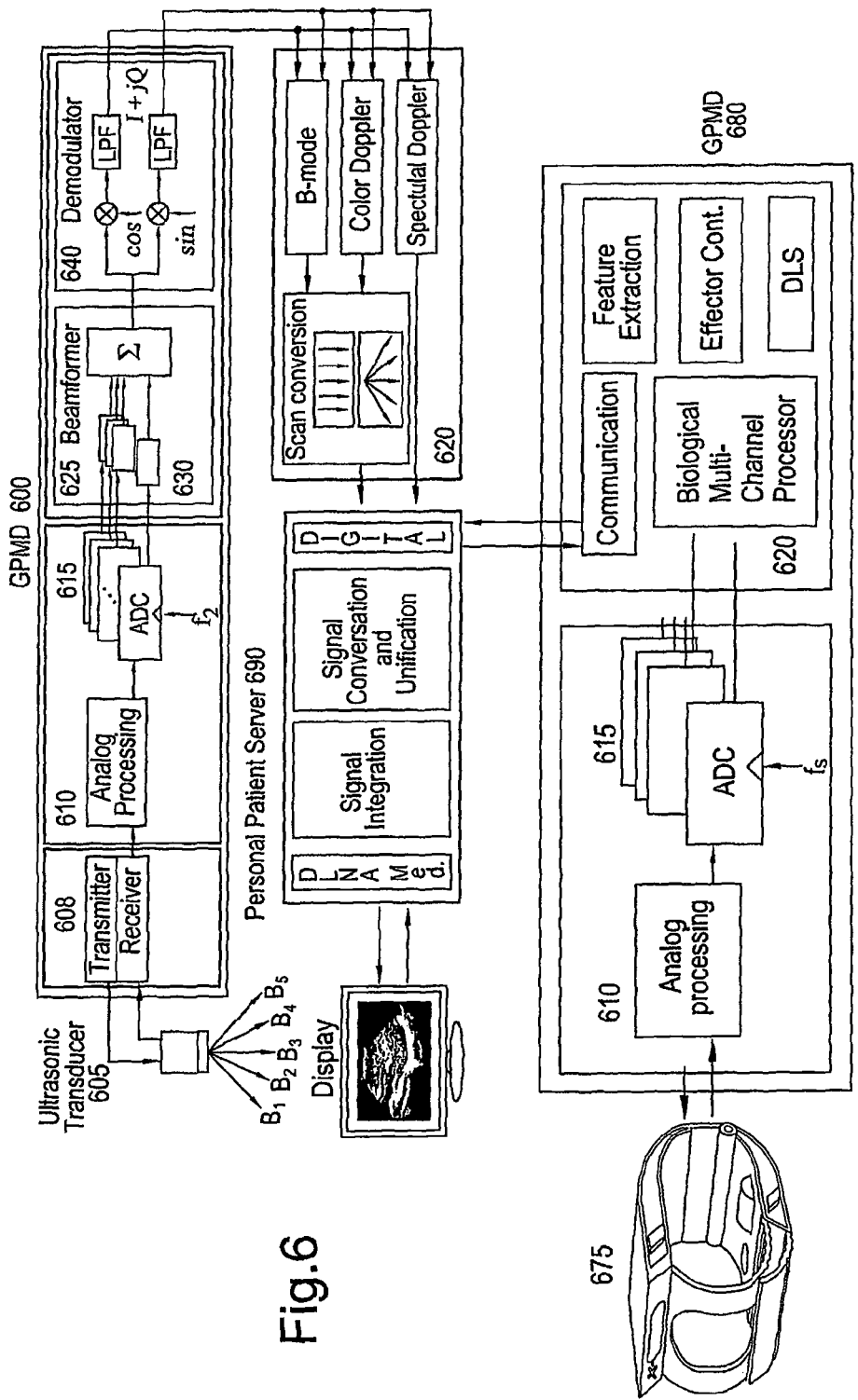
FIG. 6 shows one preferred embodiment of the inner structure of two GPMD, a complex one which is ultrasound imaging and a simple GPMD architecture used for measuring BP.

FIG. 6 shows an example of multi-tasking implementations of the GPMD. In this example, two devices are implemented and work simultaneously. The first provides, for example, ultrasound imaging capabilities and the second one provides a Continuous Non-invasive BP monitoring capability. The examples demonstrate how two devices with different types of sensors/effectors can be simultaneously emulate on the GPMD device, provided that it has sufficient computing power to handle both tasks simultaneously. Since the Continuous BP monitoring may typically operate at a slow sampling rate and needs relatively low processing power compared to the ultrasound imaging, the GPMD may further be able to provide this medical device functionality in addition to a more computationally expensive task such as 3D Echocardiography, thereby handling both 2D echocardiography and Continuous BP monitoring at the same time. 2D echocardiography with Doppler can be sufficient for continuous monitoring of Cardiac Output, after the same GPMD performed 3D echocardiography to get the initial positioning of the 2D image and the calibration of the 2D image to left-ventricle volume. This shows a possible sequence in time using the same GPMD with a 3D probe, first as 3D Echocardiographic imaging and then as 2D echocardiograph, releasing surplus computing power for the Continuous BP monitoring.

In some embodiments smart sensors and effectors may be used that further include additional functionality specific to that sensor/effector. For example, an ultrasonic probe may need dedicated a beam forming array, and if it is a mechanical 3-D scanning head, it will need the motor for it in addition to what is needed for B-scan (2-D imaging ultrasound).

In another embodiment the GMPD includes a Data Acquisition module to provide some or all of the analogue front-end, the ADC array and as much as possible general purpose hardware and software necessary to emulate a wide range of medical devices.

In this case of the IEEE 1451.4 (or later version) Sensors, the Plug & Play standard for measurement and automation can be employed detect and automatically configure sensors (an example being via Transducer Electronic Data Sheets (TEDS)). This technology provides:

Reduced configuration time by eliminating manual data entry.

Better sensor tracking by storing data sheets electronically.

Improved accuracy by providing detailed calibration information.

Simplified asset management by eliminating paper data sheets.

Reliable sensor location by identifying individual sensors electronically.

Use of "Sensors Plug&Play" hardware and software means that smart TEDS sensors can be automatically configured by a GPMD, meaning that manual sensor configuration is not necessary.

In FIG. 6 we can see two GPMD: a first configured as an ultrasound imaging GMPD designated as 600 and the second GPMD 680 for measuring BP.

We can see that both consist of an analogue part that contains the analogue processing or signal conditioning 610 and the bank of ADC 615. They also contain a processor board 620 that contain the processor, communication, memory etc. These features are implemented in the digital domain on the processor, which may be a multi-core processor as explained below.

As for software, each one of the two GPMD 600 and 680 includes different software modules according to the different needs of the two applications. In the ultrasonic imaging GPMD 600, the main modules that are specific for this application are the B-Mode, the Colour Doppler and the spectral Doppler, as well as conversion from the polar coordinate scan done by the probe phased array to a rectangular coordinates scan needed for display.

In the BP application, the specific modules are the Biological Signal Processing that includes detection of the pulses waveforms, feature extraction from the pulse shape (Pulse Wave Analysis), controlling of the effector that applies pressure on the cuff or repositioning of the pressure sensor.

Kerem Karadayi et al. in their article: "Software-based Ultrasound Beamforming on Multi-core DSP" show an algorithm to perform digital beamforming using a multi-core DSP. Beamforming is essential for attaining good image quality by increasing signal-to noise ratio (SNR), improving spatial resolution and reducing side-lobe artefacts. Digital beamforming is a compute-intensive task in modern ultrasound systems. As a result, it has traditionally been supported by hardwired architectures (e.g., with application specific integrated circuits (ASICs)). Due to the recent trend of programmable processors going multi-core, it is possible to support this compute-intensive digital beamforming in software on these multi-core architectures. They demonstrate the feasibility of supporting digital beamforming on one of Texas Instruments' (TI) C66x multi-core processors.

Figure 7:
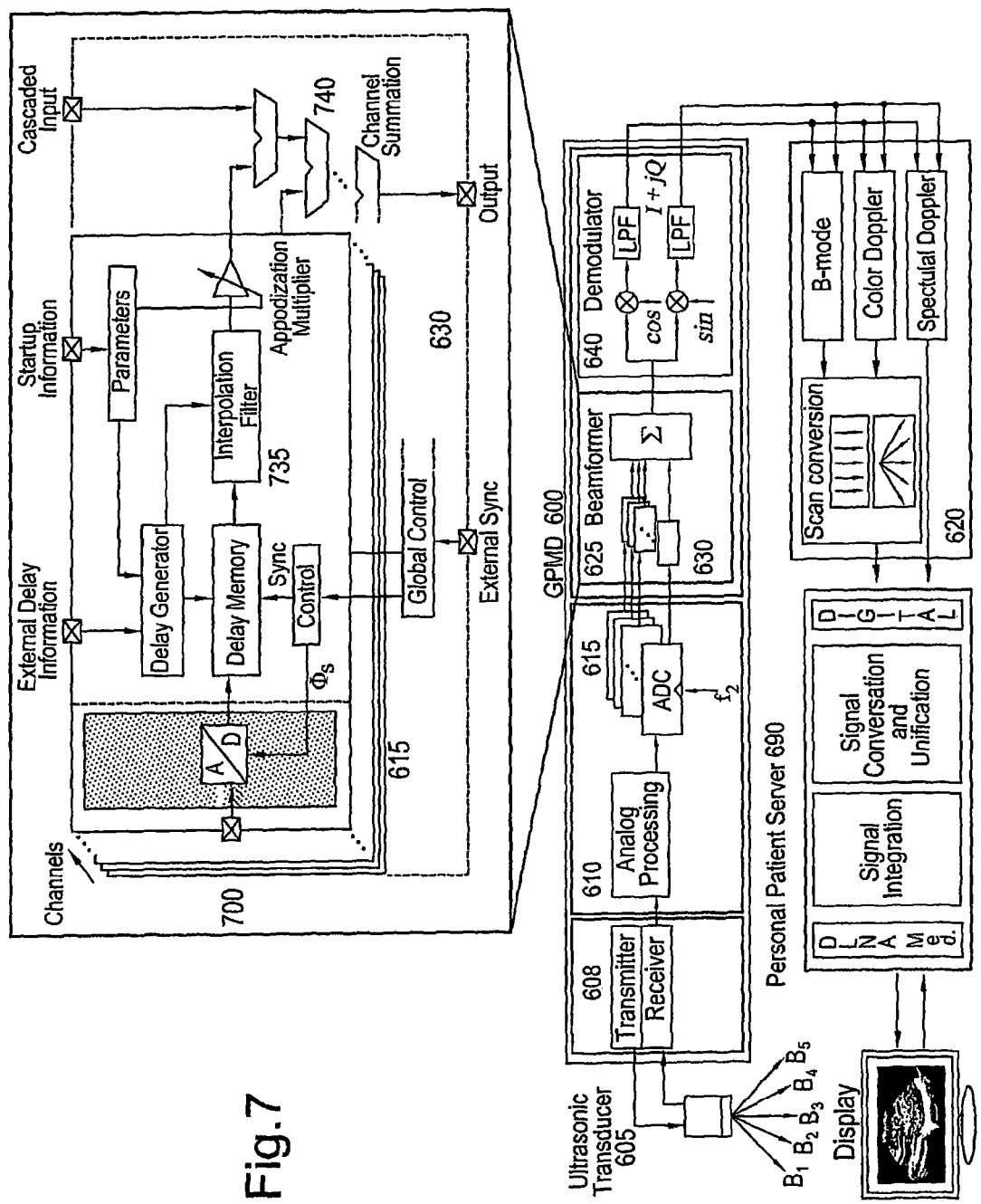
FIG. 7 shows a more detailed block diagram for the beamformer in the ultrasound imaging block diagram of FIG. 6.

FIG. 7 depicts a more detailed block diagram of the beamformer 630. It shows the ADC bank 615 that provides inputs to the beamformer. The number of inputs is corresponding to the number of elements in the ultrasonic probe and is in powers of 2, normally 64, 128 or even 256 for a 2D imaging (1D array sensor). For 3D imaging a 2D array might include several thousand or more elements.

The delay lines in a digital beamformer consist of delay generator and delay memory, as shown in FIG. 7. It can be implemented either by FPGA chip, ASIC or one or more DSPs (or a multi-core DSP). An example implementation today would be to use a DSP, such as a TI C66x 8 core DSP. Thus the GPMD may include one or more date engines/DSPs configurable to implement mathematically intensive tasks. This may be used in addition to the general purpose processor.

To provide such functionality in a GPMD and support newer more advanced algorithms, the GPMD is also upgradeable, by adding or replacement new hardware modules (such as processors) to be installed, as well as enabling the software to be upgrade to cater for new algorithms and more efficient algorithms.

Features and Capabilities of the GPMD: Further Details
Configurable Functionality:

The GPMD can change its functionality according to the software libraries uploaded to it and the choice of the sensors and effectors connected. The software libraries may not necessarily always need to be uploaded; there may be several stored configurations which can be selected, either manually or automatically depending on the sensors and/or effectors connected. Uploading of new medical device functionality, not previously installed may be via many different methods, such as network download (wired or wireless), or via a memory type device such as USB flash drive, memory card, and the like. It will be appreciated however that many alternatives are also possible, including uploading the medical device functionality from a Patient Server (medical console) previously discussed, which may have stored data, including general purpose medical device functionality, applicable for a particular patient.

The software library may include a library of signal processing functions that are used by one or more medical devices. These may be specific for a particular sensor or effector device, or functionality may be transferrable between different sensors and effectors enabling code reuse. Examples include imaging capabilities, ultrasound imaging such as beam-forming and apodization.

A GPMD may also provide robust computing features so that it does not fail when performing a critical task during use; otherwise a patient's life could be put at risk. This is a different requirement to conventional computing devices such as a PCs or smartphones. If a malfunction causes data loss or corruption, the GPMD might make an error that is unacceptable for a medical device. This therefore means both hardware and software design made need to consider such issues, and provide the necessary features to provide such robustness depending on the range of devices that the GPMD may wish to replace.

Figure 8:
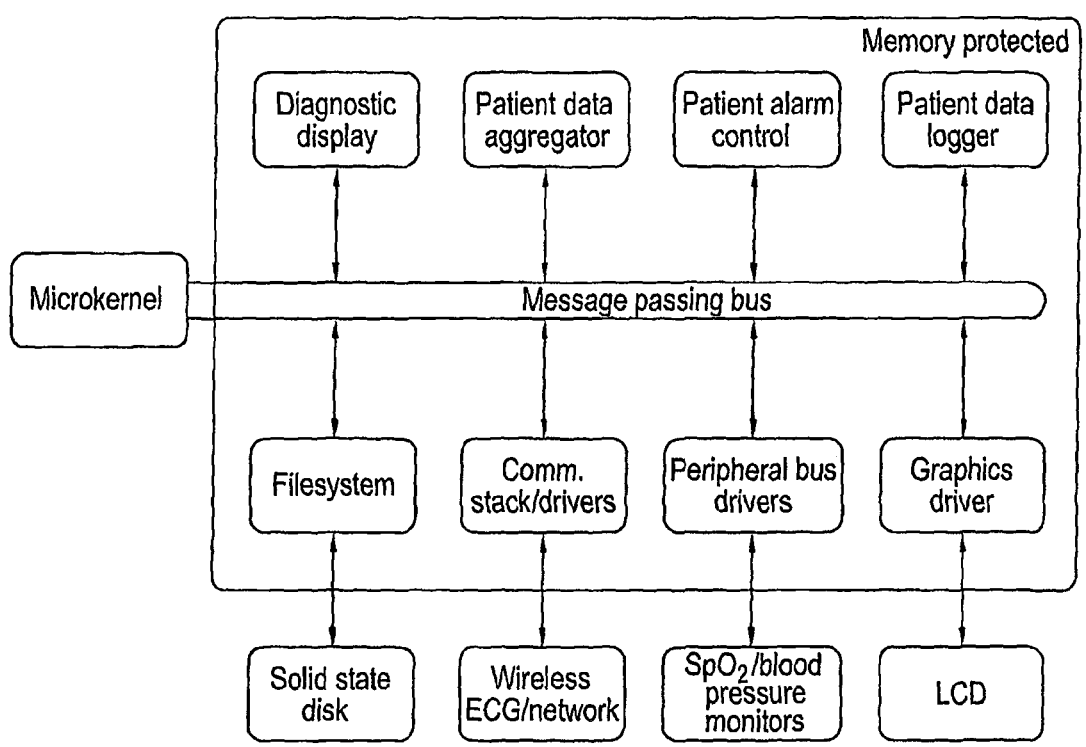
FIG. 8 shows an example of a micro-kernel operating system.
Figure 9A:
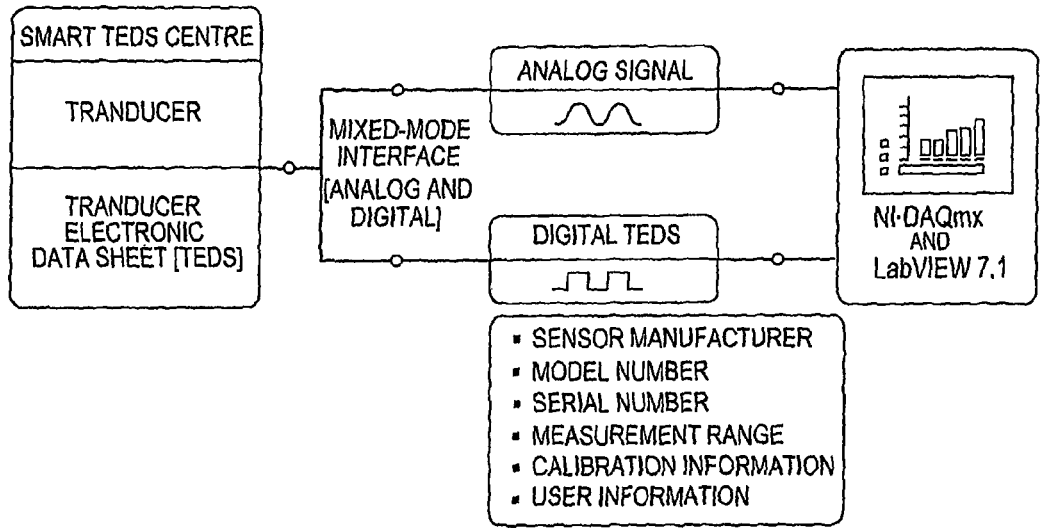
FIGS. 9a and 9b show examples of the sensors plug and play (TEDS) architecture.
Figure 9B:
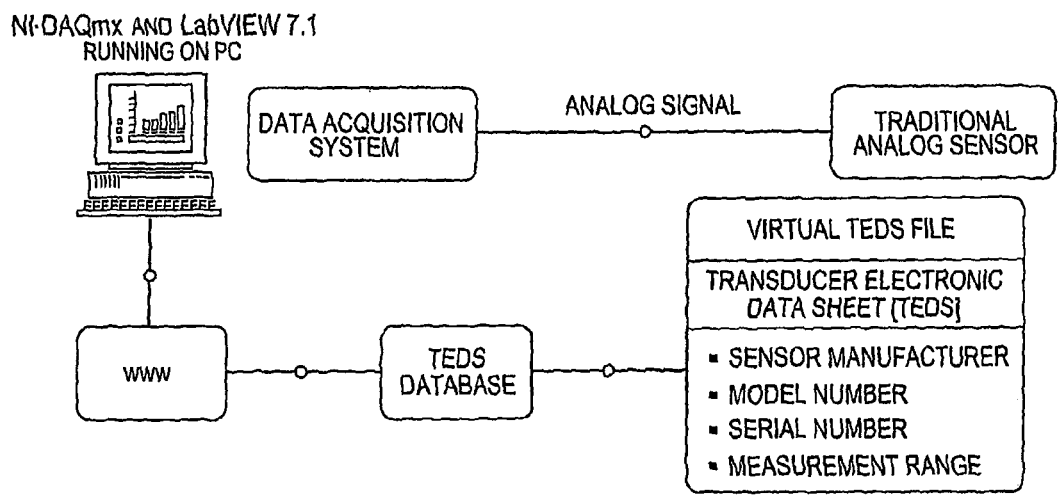

One aspect of the software that can be important for the GPMD is the operating system used, in particular if there is a desire to implement multiple medical devices at the same time. The operating system is thus preferably a real time operating system (RTOS). The GPMD may use, for example, a microkernel RTOS whereby device drivers, file systems, networking stacks, and applications all reside outside the kernel in separate address spaces. They are thus isolated from both the kernel and each other. If a fault occurs, a fault in one component will not bring down the entire system. Memory faults in a component cannot corrupt other processes or the kernel, and the OS can automatically restart any failed component without a system reboot. A micro-kernel OS in a patient-monitoring system is shown in FIG. 8.

A pre-emptible kernel is one option for a GPMD so that it meets real-time commitments, particular for the critical tasks. For instance, an emergency alarm triggered when a patient ECG stops should be able to preempt processes drawing a display, as should processes required to send out the alarm. A task, such as the display of a meal reminder matters much less, and it does not matter if these alerts are delayed when compared with a medical emergency, such as if a person's heart has stopped beating. The alarm and communications stack should have a higher priority access to CPU cycles.

A low-priority task should not prevent a higher-priority task from completing its work. For example, in a patient-monitoring system where the alarm control, data logger, and data aggregator share a resource, the higher-priority task (alarm control) must wait for the lower-priority task (data logger) to complete before it can continue. A third task (data aggregator) has a lower priority than the alarm control, but a higher priority that the data logger. The data aggregator preempts the data logger, effectively preempting the alarm control, which can no longer meet its real-time commitments. This may be addressed, for example, in the GPMD using priority inheritance techniques to prevent priority inversions by assigning the priority of a blocked higher-priority task to the lower-priority thread doing the blocking until the blocking task completes. For example, the data logger inherits the alarm control's priority, and hence can't be preempted by the data aggregator. When it completes, it reverts to its original priority, and the alarm control unblocks and continues, unaffected by the data aggregator. As a further example, a heart monitor that loses connectivity may cause a central monitoring system to incorrectly assume an alarm condition and dispatch help, or—far worse—the patient may be in distress with no one alerted and no help forthcoming.

Resource partitioning is one technique that may also be used in the GPMD RTOS. With fixed partitioning, the system designer divides tasks into partitions, allocating a portion of CPU time to each. No task in any partition may consume more than that partition's percentage of CPU time. If such a mechanism is implemented, it will be appreciated that if the GPMD is configured to run as more than one device, the processor in the GPMD must be able to meet the necessary targets.

Other features that may be provided in the GPMD include a watchdogs (software and hardware), that monitors the system and performs multi-stage recoveries, clean shutdowns and/or alerts to operators as appropriate for the particular configured functionality and criticality of the operation being performed.

Multicore Support

With the complexity of tasks that the GPMD could perform, some embodiments may use multi-core processors to meet the processing demands of, for example—medical imaging systems.

As more sophisticated imaging and measurement technologies become available, more and more medical devices of all kinds will need multi-core processing just to handle the data they receive. Remote-care devices, even devices for use in the home by the patients themselves, are no exception. The aging populations of industrialized countries suggest a growth in the need for in-home and personal devices that support sophisticated monitoring activities coupled with simple interfaces. Thus, even if a manufacturer's current devices do not require multi-core processing, future devices almost certainly will.

When coupled to multiple sensors and/or effectors, the GPMD can also function as more than one medical device at the same time. As will be appreciated, there may be a limit on the number of medical devices that the GPMD can replace at any one time, based on processing requirements, interface limitations and real-time requirements of any particular device. Implementations may, for example, harness the multicore capabilities of a microprocessor in the GMPD such that each device runs on one or the cores in the multicore processor. Alternatively an operating system may be used which can allocate the device functions dynamically to one or more of the cores using task scheduling techniques known in the art. Core and/or thread level parallelism may then be adopted according to the available functionality within processing elements within the GPMD. Furthermore, multicore architectures may be particularly useful when any task is computationally expensive, such as beam-forming. Being able to distribute tasks over multiple cores can be particularly useful in such situations.

Some GPMDs may also be upgradeable, for example, via replacement processing modules, to allow increased processing capabilities to be provided as and when improved performance microprocessors, DSPs, and the like become available.

Interfacing with, and Control of, Sensors and Effectors:

The GPMD may communicate with any of the sensors, effectors, and Patient Server by wired or wireless communications, using any known communications standards. If any sensors are adjustable, such as those previously described, then the GPMD can adjust such sensors accordingly based on the configuration of the GPMD and the task it is setup to perform within the connected sensors. 1. This may include controlling automatically adjustable medical sensors that include at least one sensor, and controlling effectors that can change position, orientation and/or pressure under external control of the GPMD. Examples include sensors for monitoring blood flow velocity, viscosity, coagulation factor, glucose concentration to optimize accuracy and noise robustness and cut costs of the individual devices.

The GPMD may deal with one channel or multi input channels of the same type (e.g., ECG, EEG). As a GPMD can emulate more than one device, this may lead to, in effect, the GPMD acting as several separate independent devices.

With a multichannel input, the GMPD may also provide capabilities to receive data from multiple sensors. This means that, with the appropriate software libraries running, data from multiple sensors may be received and combined to improve data acquisition. The GPMD may provide the functionality of one device (e.g., BP measurement, ECG, EEG, ultrasonic Imaging) at any one time. However, as it may also provide the functionality of more than one device, thus exposing several devices or services, the data from these 'multiple devices' may be combined. This may be done, for example, at a connected Patient Server device. At the Patient Server, data from the multiple channels may be combined to provide a 'noise reduced' signal, or alternatively, may be used to derive a new parameter.

Interaction with a Patient Server

The GPMD can communicate and interact with the Patient Server. This may include, delivering signals and data to the Patient Server for storage, analysis, combination. If the data originated from sensors, then this may subsequently lead to the Patient Server providing control over effector devices. These sensor and effector devices can each be GPMDs.

Connecting to a Patient Server may remove the need for a GPMD to have, for example, a graphical display or user control interface. Providing ECG or imaging device functionality for example, the GPMD could deliver the display data to a Patient Server to display. Similarly, coupled to a Patient Server, a user interface/input source (keypad, touchscreen, and the like) could be provided by the Patient Server and control data communicated to the GPMDs. As functionality is changed on a GPMD, via automatic detection technologies such as "plug and play" (PnP), the Patient Server can automatically become aware of any change in connected GPMD functionality.

Figure 10:
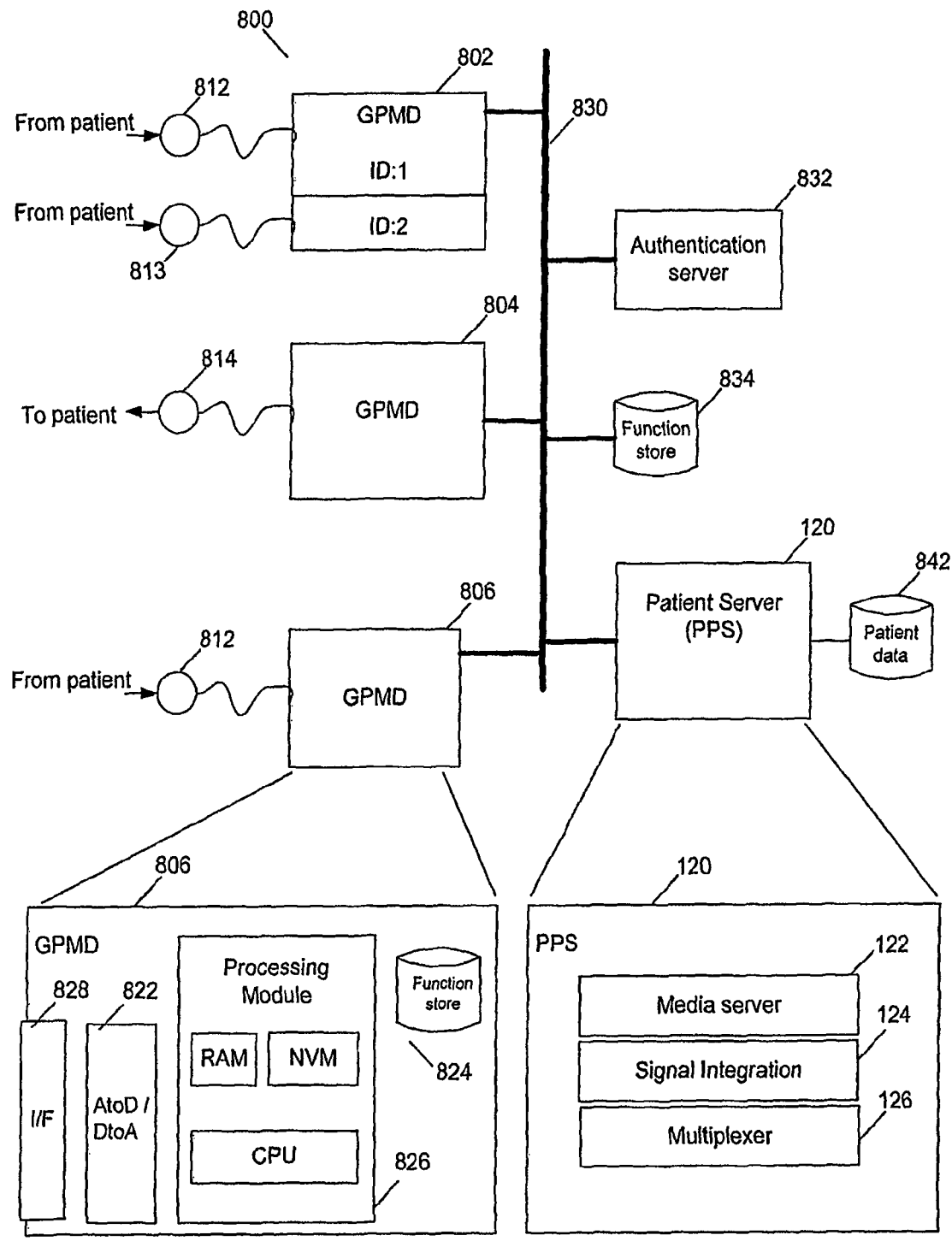
FIG. 10 shows an example of the complete system for capturing and processing data, including a Patient Server and several General Purpose Medical Devices.

FIG. 10 shows an example patient data capture, control and processing system 800 incorporating multiple GPMDs (programmable platform medical devices) in communication with a personal Patient Server (PPS).

System 800 comprises three GPMDs 802, 804, and 806, a PPS 120, an authentication server 832, and function data store 834. The components are connected by a communications connection 830, which may be any one of many different connection standards including a network (wired or wireless), USB, and the like.

GPMDs 802, 804, and 806 each comprise (as illustrated for GPMPD 806) an interface 828, such as a sensor interface, for connection to a sensor 816 attached to a patient. Analogue to digital conversion may also be present if conversion to digital data is not provided directly in the sensor 816. For providing control output, as provided by GPMD 804 and controller 814, digital to analogue conversion may be required if any device being controlled (e.g., for the administration of a substance to a patient), requires analogue control signals. The processing module 826 includes a CPU (e.g., multi core CPU), RAM and one or more variants of non volatile memory, e.g., flash, a hard disk, and/or ROM which can be used to store the operating system for the GPMD.

Optionally, the GMPD also includes a function data store 824 which stores a plurality of different patient sensing/control functions allowing the GPMD to take on the role of one or more different medical devices. In variants, however, the function store may be managed centrally, either in the Patient Server 120 or as a separate data store 834 connecting to the communications connection/network. Providing a separate function store that is accessed by the GPMDs allows central control, updating, and management of the content.

In the example in FIG. 10, GMPD 802 is configured to operate as two separate medical devices, device ID:1, and device ID:2, each connected to separate sensors 812 and 813 to provide different sensing functions.

The Patient Server (medical console/PPS) includes a media server 122, signal integration and control module 124, and multiplexer 126.

A DLNA Media Server 122 may be used to provide a server for rendering video signals. The Patient Server 120 is able to process such signals in order to convert them into an appropriate format for visualization. In order for the Patient Server to be able to use a DLNA Media Renderer (e.g., DLNA TV), the signals may be converted to a video stream by the media server 122 to allow rendering by a connected DNLA media display device.

The multiplexer module 126 interfaces to the communications connection and communications with the various GPMDs around the patient. Signal integration and control module 124 receives the multi-channel information from the various GPMDs, using multi-channel models to generate the signals to be displayed and/or employs control algorithms to control effectors such as an Infusion Pump (which GPMD 814, for example, may be configured to provide back end processing for a mechanical pump front end 814).

Signal integration in the Patient Server may be used to combine/integrate signals from multi sensors and effectors, which can be used to filter clinically significant events from the GPMDs to detect clinically significant events. The generated/collected data may then be stored in the patient data records 842.

No doubt many other effective alternatives will occur to the skilled person. It will be understood that the invention is not limited to the described embodiments and encompasses modification apparent to this skilled in the art lying within the spirit and scope of the claims appended hereto.

The invention claimed is:

1. A patient data capture and processing system, the system comprising:
   at least one general programmable medical device (GPMD) comprising:
   a plurality of sensors;
   a plurality of effectors for interrogation, treatment, or interrogation and treatment, wherein each effector is selected from the group consisting of an ultrasound probe scanning motor, an infusion pump, a ventilator, an inflated bladder provided on a wrist assembly, a roller coupled with a step-motor, a drug delivery pump, a breathing apparatus, and any combination thereof;
   a processing module coupled with memory, interfacing with the plurality of sensors and the plurality of effectors and to a communications connection; and
   a function data store used by the processing module to define a plurality of different automatically adjustable sensor (AAS) functions for emulating a plurality of different medical devices, wherein the function data store is controlled via the communications connection, wherein said memory retains programs operative to cause the processor module to provide duties selected from the group consisting of automatically adjusting the effectors, data acquisition from the sensors and the effectors, actuating the effectors, transmitting the data over the communications connection, retrieving additional programs, and any combination thereof; and
   a patient medical device controller (PPS) comprising:
   a patient server connected to said communications connection; and
   patient data records coupled to the patient server,
   wherein the patient server is configured to program the function data store of the GPMD, and obtain the data acquired by the GPMD via the communications connection, wherein the data is stored in patient data records, and wherein the patient server is further configured to extract and output clinically significant events.

2. The system of claim 1, wherein the plurality of different medical devices is selected from the group consisting of continuous and temporal blood pressure monitoring; ECG; monitoring of arterial blood chemical properties; drug delivery device; stethoscope, temperature, bio impedance, blood flow; and any combination thereof.

3. The system of claim 1, wherein the function data store comprises a plurality of different sensing and control functions enabling the GPMD to emulate one or more different medical devices.

4. The system of claim 1, wherein the GPMD emulates at least two devices of the plurality of different medical devices simultaneously.

5. The system of claim 1, wherein the at least one sensor is selected from the group consisting of pressure sensors; force sensors; optical sensors; accelerometers sensors; bio-impedance sensors; acceleration and gyro sensors; doppler sensors; sound sensors; analogue electrodes; piezo-array sensors; temperature sensors; voltage sensors; thermocouples; and any combination thereof.

6. The system of claim 1, wherein at least one sensor of the plurality of sensors and at least one effector of the plurality of effectors are embedded within a wearable object.

7. The system of claim 1, wherein the GPMD further comprises front-end electronics for said data acquisition from the sensors.

8. The system of claim 1, wherein the memory further comprises control algorithms for actuating the effectors.

9. The system of claim 8, wherein the processor module utilizes the control algorithms and data acquired from the sensors in order to incrementally actuate a given effector for aligning an adjustable sensor to optimal data acquisition position, wherein the given effector is associated with an adjustable sensor.

10. The system of claim 1, wherein the PPS is provided within a cloud computing server and wherein the communications connection between the PPS and the GPMD utilizes internet connection.

11. The system of claim 1, wherein the patient data records are deployed as cloud storage and wherein communications between the PPS and the patient data records utilizes internet connection.

12. The system of claim 1, wherein the system is dedicated to one patient and situated around the patient and wherein the PPS is further configured to control the effectors and wherein the PPS further comprises a user's interface device capable of exchanging information associated to a patient with a user.

13. The system of claim 12, wherein the PPS is capable of being controlled remotely by a telemedicine application.

14. A patient data capture and processing system, the system comprising:
- at least one general programmable medical device (GPMD) comprising:
  - at least one sensor and at least one imaging sensor, wherein the imaging sensor is selected from the group of imaging sensors consisting of ultrasound, MRI, CT, and X-ray, acting as an automatically adjustable sensor (AAS) that is responsive to a patient medical condition;
  - a processing module coupled with memory, interfacing with the at least one sensor and the at least one imaging sensor and to a communications connection; and
  - a function data store used by the processing module to define a plurality of different AAS functions for emulating a plurality of different medical devices, wherein the function data store is controlled via the communications connection,
  - wherein said memory retains programs operative to cause the processor module to provide duties selected from the group consisting of automatically adjusting the at least one imaging sensor; data acquisition from the at least one sensor and the at least one imaging sensor; actuating the imaging sensor; transmitting the data over the communications connection; retrieving additional programs; and any combination thereof; and
- a patient medical device controller (PPS) comprising:
  - a patient server connected to said communications connection; and
  - patient data records coupled to the patient server,
  - wherein the patient server is configured to program the function data store of the GPMD, and obtain the data acquired by the GPMD via the communications connection, wherein the data is stored in patient data records, and wherein the patient server is further configured to extract and output clinically significant events.

15. The system of claim 14, wherein the plurality of different medical devices is selected from the group consisting of ultrasound imaging; ECG; monitoring of arterial blood chemical properties; drug delivery device; stethoscope, temperature, bio impedance, blood flow; and any combination thereof.

16. The system of claim 14, wherein the function data store comprises a plurality of different sensing and control functions enabling the GPMD to emulate one or more different medical devices.

17. The system of claim 1, wherein the GPMD emulates at least two devices of the plurality of different medical devices simultaneously.

* * * * *